US011413279B2

(12) United States Patent
Murdock et al.

(10) Patent No.: US 11,413,279 B2
(45) Date of Patent: Aug. 16, 2022

(54) METHODS AND COMPOSITIONS FOR THE ANTIVIRAL USE OF SYNTHETIC LYSINE ANALOGS AND MIMETICS

(71) Applicant: Anti-Viral Technologies, LLC, Dallas, TX (US)

(72) Inventors: Frank Murdock, Dallas, TX (US); Ronnea Murdock, Dallas, TX (US); W. Paul Stewart, Dallas, TX (US)

(73) Assignee: Anti-Viral Technologies, LLC, Dallas, TX (US)

( * ) Notice: Subject to any disclaimer, the term of this patent is extended or adjusted under 35 U.S.C. 154(b) by 0 days.

(21) Appl. No.: 16/610,504

(22) PCT Filed: Aug. 9, 2018

(86) PCT No.: PCT/US2018/046023
§ 371 (c)(1),
(2) Date: Nov. 2, 2019

(87) PCT Pub. No.: WO2019/045989
PCT Pub. Date: Mar. 7, 2019

(65) Prior Publication Data
US 2020/0323837 A1 Oct. 15, 2020

Related U.S. Application Data

(60) Provisional application No. 62/664,555, filed on Apr. 30, 2018, provisional application No. 62/550,656, filed on Aug. 27, 2017.

(51) Int. Cl.
| | |
|---|---|
| *A61K 31/454* | (2006.01) |
| *A61P 31/22* | (2006.01) |
| *A61K 31/195* | (2006.01) |
| *A61K 31/197* | (2006.01) |
| *A61K 9/00* | (2006.01) |
| *A61K 9/127* | (2006.01) |

(52) U.S. Cl.
CPC .......... *A61K 31/454* (2013.01); *A61K 9/0014* (2013.01); *A61K 9/0019* (2013.01); *A61K 9/0024* (2013.01); *A61K 9/0043* (2013.01); *A61K 9/0053* (2013.01); *A61K 9/127* (2013.01); *A61K 31/195* (2013.01); *A61K 31/197* (2013.01); *A61P 31/22* (2018.01)

(58) Field of Classification Search
CPC ....................................................... A61P 31/22
See application file for complete search history.

(56) References Cited

U.S. PATENT DOCUMENTS

| | | | |
|---|---|---|---|
| 2004/0048327 A1 | 3/2004 | Powers et al. | |
| 2012/0082677 A1* | 4/2012 | Abdul Aziz | A61K 38/45 424/150.1 |
| 2014/0271923 A1* | 9/2014 | Reid | A61K 31/496 424/651 |

FOREIGN PATENT DOCUMENTS

| | | | | |
|---|---|---|---|---|
| EP | 1057490 A2 | 12/2000 | | |
| WO | WO-0037071 A1 * | 6/2000 | ............... | A61K 8/44 |
| WO | WO-2004/032915 A1 | 4/2004 | | |
| WO | WO-2004032915 A1 * | 4/2004 | ........... | A61K 31/195 |

OTHER PUBLICATIONS

Harvard Health Newsletter, found online at https://www.health.harvard.edu/diseases-and-conditions/by_the_way_doctor_does_lysine on Dec. 31, 2020. Dated Mar. 2007 (Year: 2007).*
Ruth F Itzhaki, S Louise Cosby, and Matthew A Wozniak. Herpes simplex virus type 1 and Alzheimer's disease: The autophagy connection. Journal of NeuroVirology, 14: 1-4, 2008), (Year: 2008).*
T. Dubrovina, et al. "Protective activity of -aminocaproic acid in influenza: mechanisms of action," Nov. Podkhody Khimioter. Virusn. Infekts. (1991), 154-61. In Russian; abstract provided. (Year: 1991).*
E.S. Gershom, et al. "Herpesviruses enhance fibrin clot lysis," Thromb Haemost 2012; 107: 760-768. (Year: 2012).*
Wiki article "Tranexamic acid". Downloaded Jan. 2, 2021 from https://en.wikipedia.org/wiki/Tranexamic_acid (Year: 2021).*
NIH: Preventing Alzheimer's disease. Found online at https://www.nia.nih.gov/health/preventing-alzheimers-disease-what-do-we-know on Dec. 31, 2020 (Year: 2020).*
Merriam Webster definition of "analogue," downloaded Downloaded Dec. 31, 2020 from https://www.merriam-webster.com/dictionary/analogue (Year: 2020).*
Merriam Webster definition of "derivative," Downloaded Oct. 26, 2018 from: https://www.merriam-webster.com/dictionary/derivative (Year: 2018).*
Google scholar search Dec. 30, 2020 (Year: 2020).*
Google scholar search Dec. 31, 2020 (Year: 2020).*
M. Gerstein, et al. Left ventricle thrombus after tranexamic acid for spine surgery in an HIV-positive patient. The Spine Journal 16 (2016) e77-e82. (Year: 2016).*
T. Naito, et al. Antiviral effect of arginine against herpes simplex virus type 1 International Journal of Molecular Medicine 23: 495-499, 2009. (Year: 2009).*

(Continued)

*Primary Examiner* — Michael P Cohen
(74) *Attorney, Agent, or Firm* — Winstead PC

(57) ABSTRACT

A method for treatment, prevention, or reduction of one-time or recurring viral outbreaks, for suppression of development or growth of chronic viral infections, or for prevention or treatment of viral infections, the method including, administering a synthetic lysine analog or mimetic, where the synthetic lysine analog or mimetic antagonizes or competes with an amino acid or other biological agent required by a virus to replicate or spread. Additionally, a composition to treat, prevent, or reduce one-time or recurrent viral outbreaks, suppress development or growth of chronic viral infections, or to prevent or treat viral infections, the composition including, a synthetic lysine analog or mimetic, where the synthetic lysine analog or mimetic antagonizes or competes with an amino acid or other biological agent required by a virus to replicate or spread.

11 Claims, No Drawings

(56) References Cited

OTHER PUBLICATIONS

SciFinder_search_Nov. 2, 2021_tranexamic_acid_and_anti-viral. pdf (Year: 2021).*

SciFinder_search_Nov. 4, 2021_E-aminocaproic_acid_antiviral.pdf (Year: 2021).*

J. Bostrom, et al. "Potent Fibrinolysis Inhibitor Discovered by Shape and Electrostatic Complementarity to the Drug Tranexamic Acid,"J. Med. Chem. 2013, 56, 3273-3280. (Year: 2013).*

V.P. Lozitsky ("Anti-Infectious Actions of Proteolysis Inhibitor e-Aminocaproic Acid (e-ACA)," National Institute of Allergy and Infectious Diseases, NIH vol. I, Frontiers in Research, Edited by: Vassil St. Georgiev, Karl A. Western, and John J. McGowan, Humana Press. Totowa, NJ, 2008, 193-198). (Year: 2008).*

Espacenet_search_Jan. 24, 2022_aminocaproic_acid_and_antiviral. pdf (Year: 2022).*

Espacenet_search_Jan. 24, 2022_tranexamic_acid_and_antiviral. pdf (Year: 2022).*

Machine_Translation_WO2004032915_tsunoda (Year: 2022).*

International Search Report and Written Opinion of the International Search Authority, dated Oct. 2, 2018 by Authorized Officer Shane Thomas.

Lozitsky, V. et al.; "Anti-influenza Efficacy of Combination Apply of Proteolytic Inhibitor E-aminocaproic Acid with Neuraminidase Inhibitor Tamiflu"; Anitviral Research; vol. 82 No. 2; May 1, 2009; p. A34.

Kutty, Raja K et al.; "Convservative Treatment of Chronic Subdural Hematoma in HIV-Associated Thrombocytopenia with Tranexamic Acid"; Journal of the International Association of Providers of AIDS Care; vol. 16 No. 3; May 2017; pp. 211-214.

Ollier, Laurence et al.; "High Permissivity of Human HepG2 Hepatoma Cells for Influenza Viruses"; Journal of Clinical Microbiology; vol. 42 No. 12; Dec. 2004; pp. 5861-5865.

* cited by examiner

METHODS AND COMPOSITIONS FOR THE ANTIVIRAL USE OF SYNTHETIC LYSINE ANALOGS AND MIMETICS

CROSS-REFERENCE TO RELATED APPLICATIONS

This patent application claims priority from, and incorporates by reference the entire disclosure of, U.S. Provisional Patent Application No. 62/550,656 filed on Aug. 27, 2017 and U.S. Provisional Patent Application No. 62/664,555 filed on Apr. 30, 2018.

BACKGROUND

Technical Field

The present disclosure relates generally to lysine analogs and mimetics and more particularly, but not by way of limitation, to methods and compositions for the antiviral use of synthetic lysine analogs and mimetics.

History of Related Art

Herpes Simplex Virus Type 1 (HSV-1) and Herpes Simplex Virus Type 2 (HSV-2) are very common viruses in the human population with various estimates indicating that up to 80% of the world's population are carriers of HSV-1. Similarly, the U.S. Centers for Disease Control and Prevention estimates that approximately 99.5% of people born in the United States who are 40 years of age and older have been infected with wild-type varicella-zoster virus (VZV). In addition to HSV-1, HSV-2, and VZV, it is estimated that approximately 36.7 million people are currently living with the Human Immunodeficiency Virus (HIV). While many people worldwide suffer from HSV-1, HSV-2, VZV, and HIV, cold and influenza viruses are even more prominent, and can have severe or life-threatening effects on various age groups or persons susceptible to viral infections. One approach to treatment is the use of antiviral medications, though several antiviral medications show limited to no efficacy in treatment, prevention, and suppression of HSV-1, HSV-2, VZV, HIV, or cold and influenza viruses.

SUMMARY OF THE INVENTION

A method for treatment, prevention, or reduction of one-time or recurring viral outbreaks, for suppression of development or growth of chronic viral infections, or for prevention or treatment of viral infections, the method including, administering a synthetic lysine analog or mimetic, where the synthetic lysine analog or mimetic antagonizes or competes with an amino acid or other biological agent required by a virus to replicate or spread.

A composition to treat, prevent, or reduce one-time or recurrent viral outbreaks, suppress development or growth of chronic viral infections, or to prevent or treat viral infections, the composition including, a synthetic lysine analog or mimetic, where the synthetic lysine analog or mimetic antagonizes or competes with an amino acid or other biological agent required by a virus to replicate or spread.

DETAILED DESCRIPTION

Examples of viruses that remain chronically in the human body and exhibit recurrent outbreaks are Herpes Simplex Virus Type 1 (HSV-1) and Herpes Simplex Virus Type 2 (HSV-2) which are very common viruses in the human population. HSV-1 is usually associated with cold sores, or recurrent herpes labialis (RHL), but HSV-2 can also be involved. HSV-2 is usually associated with genital herpes, but likewise HSV-1 can also be involved. HSV-1 is more common, with various estimates indicating that up to 80% of the world's population carries the HSV-1 virus due to its highly contagious nature, and as many as 40% of the global population have regularly recurring RHL outbreaks. There is typically no sign a person carries a herpes virus until an outbreak occurs, which in the case of RHL, commonly affects the lips or the region near the mouth. The visible outbreak can take the form of sores which become inflamed and are potentially unattractive and painful. The course of the virus' outbreak and its associated visible lesions usually fully resolve via the natural healing processes of the human body, without medical treatment, over the course of approximately 2 to 4 weeks.

Current treatments designed to lessen the severity and shorten the duration of these outbreaks consist primarily of antiviral drugs, such as VALTREX® which is an oral treatment, and ABREVA® which is an ointment. These treatments have been shown to be somewhat effective, but commonly the sores are still visible and symptomatic up to 2 weeks, even when used as directed at the first sign of outbreak. With respect to recurrence, as opposed to severity or healing time, a 2016 Cochrane Review found limited clinical benefit from oral antiviral medications and no efficacy, or unconfirmed efficacy, for topical antiviral medications or any other treatments.

Research has indicated that histidine and arginine, in that order, are the two most important of 11 amino acids required for the HSV-1 virus to replicate, based on a test in which viral growth was measured when each of the various amino acids was excluded from the medium. Furthermore, lysine was not required for viral replication, and in fact exhibited an inhibitory effect on viral growth. In other research, it has been shown that increasing the preponderance of lysine compared to arginine in the body suppresses replication of the virus. Thus, by changing the diet to reduce arginine-rich foods and to increase lysine-rich foods, for example, by taking lysine supplements or by administering creams or ointments containing lysine, the severity and duration of a cold sore outbreak might be reduced. Moreover, a long-term change in diet, or supplementation, might reduce the incidence of HSV-1 outbreaks. Therefore, a variety of lysine nutritional supplement products are on the market. However, from 1975 to 1987, five studies, mostly double blind, placebo-controlled parallel or crossover studies, were conducted on supplementation with oral lysine. Three of the studies found that long-term daily supplementation with lysine reduced the severity and recurrence of outbreaks, while one found that it reduced recurrence only, and one found no benefit for either severity or recurrence. Currently, the primary treatment recommended by physicians is oral and topical antiviral medications, typically on signs of an outbreak.

Furthermore, there are multiple topical creams and ointments containing lysine, such as SUPERLYSINE+™ Cold Sore Treatment, which is promoted to cut healing time in half by providing pain relief, helping to stop burning and itching, and moisturizing the infected area. However, in this product, the active ingredient is menthol and the amino acid L-lysine is listed as an inactive ingredient along with various plant based extracts, vitamins, and zinc oxide. In addition, even if the healing time is cut in half, the subject may still suffer through one to two weeks of outbreak. The clinical study in support of this product showed that almost half of the 30 subjects were not cured through the fourth day, and it required 11 days for all 30 to be cured.

Due to the commonality of HSV-1, further research has been conducted to identify, and better understand, the interactions of HSV-1 in the body to facilitate in treatment and to inhibit reoccurrence. In vitro tests show that HSV-1 has amino acid nutritional requirements, with lysine, histidine, and arginine, in particular, playing a vital role in herpetic viral replication, as briefly discussed above. However, histidine deficiency led to marked cytopathic effects, so it was not studied further, and subsequent research focused on antagonizing arginine to achieve viral inhibition without cytotoxicity.

It has been demonstrated that adding arginine to cultures of HSV-1 maintained an optimum HSV-1 viral growth level, and it has further been demonstrated that HSV-1 is dependent upon arginine for multiplication. Studies report that HSV-1 does not grow without arginine in a culture medium. In an arginine-deficient medium, HSV-1 showed inhibited virion synthesis, reduced amounts of protein synthesis, and inhibited viral peptide transport from cytoplasm to nucleus. This shows promising results to enhance both treatment and prevention of reoccurrence by relying on the arginine-dependence for reproduction.

Studies have shown that in an arginine-deficient medium, the envelope polypeptide (II) of HSV-1 is transported very slowly from cytoplasm to the nucleus. Polypeptide (VII) is an arginine-rich protein that is arginine-dependent for synthesis. Without arginine, most of the viral structural proteins, especially viral capsid polypeptide II, are left in the cytoplasm. In addition, the HSV-1-DNA in the nucleus is uncoated and unable to replicate. The remaining viral proteins in the cytoplasm are degraded rapidly.

Various studies have been conducted to verify that arginine supports HSV-1 growth and that lysine antagonizes this action of arginine in vitro. The action of lysine appears to be multifactorial. One mechanism appears to involve the histone layer around the DNA of the host eukaryotic cell. Five different types of histones have been identified and are synthesized only during DNA replication, where lysine-rich histones cross-link DNA fibrils of chromatin during metaphase and interphase, making the chromatin more compact and thus maintaining the structural integrity of the human chromosome. The DNA nucleoside composition of HSV-1 contains a higher ratio of arginine to lysine, and the infected cell synthesizes proteins of higher arginine to lysine ratio. HSV-1 makes frequent use of the guanine(G)-containing codons, whereas human host cells have infrequent use of the cytosine(C)-guanine. There are six arginine codons and only two lysine codons. A simple shift of one nucleotide produces arginine. This can occur quite rapidly in the translation apparatus of the infected host cell. Lysine-rich, host-cell proteins are altered by the viral DNA, and new arginyl, tRNA synthesizing, arginine-rich proteins are produced.

Research indicates that lysine also seems to antagonize arginine by appearing to be an antimetabolite and analog of arginine, competing for reabsorption at the renal tubules, resulting in increased arginine excretion, competing for transport across the intestinal wall, acting as an arginase inducer, resulting in degradation of arginine, and decreasing the intracellular content of arginine in the tissue cells by entering the transport system.

In addition to in vitro tests, several clinical studies have been undertaken, which indicated that, when taken in a proper dose and in the right conditions (e.g., controlling the amount of arginine-containing foods consumed), lysine taken orally for extended periods successfully reduced the recurrence of cold sore outbreaks. However, this line of research ended, possibly because of concern that continuous consumption of natural lysine might have unwanted side effects. Thus, using synthetic (man-made) lysine analogs or mimetics to mimic the antiviral effect of lysine, or to enhance the effect of natural lysine, with respect to the herpes viruses could be beneficial, including lysine analogs or mimetics delivered topically so that they affect the relevant tissues directly, with reduced systemic impact.

As detailed above, oral and topical lysine treatments have been shown to have limited benefits and the primary, physician-directed, treatment of oral and topical antiviral drugs have also shown limited efficacy in reducing severity, duration, and recurrence of HSV-1 outbreaks. However, in light of the above research and studies, a therapeutic treatment of an antiviral agent that more significantly reduces the severity and duration of the outbreak of HSV-1 would prove beneficial. Moreover, with the aid of information obtained in the various studies described in detail above, extended or prophylactic use of an antiviral agent to avoid reoccurrence of HSV-1 outbreaks would further prove beneficial.

In addition to the treatment and suppression of reoccurrence of HSV-1 outbreaks, lysine, and analogs or derivatives thereof, can prove to be beneficial for prophylactic use with other viral infections, for example, the Human Immunodeficiency Virus (HIV), influenza viruses, and cold viruses, among others. HIV is an example of a virus that remains chronically in the human body and does not exhibit outbreaks, but rather develops over time with serious adverse consequences. Ongoing replication of the HIV virus eventually destroys the immune system, leaving the body susceptible to other life-threatening diseases. Research indicates that, unlike the herpes viruses, HIV requires lysine for replication, and when lysine was added to the blood plasma of patients infected with HIV, replication of the virus was rapidly increased. On the other hand, when arginine was added, there was no effect. It is contemplated that synthetic lysine analogs or mimetics can be utilized to inhibit the replication of HIV by competing with (blocking) the activity of natural lysine, and the in vitro testing described below appears to confirm this effect.

Moreover, extended or prophylactic use of an antiviral agent to avoid infection would be beneficial, and could include, for example, influenza and cold viruses, or other transient viruses, and be especially advantageous for subjects at heightened risk for exposure to infection, such as teachers or travelers, and for individuals at greater risk of severe consequences from infection, such as the elderly or infants. Literature in the natural medicine industry indicates that supplemental lysine is beneficial in treating and avoiding influenza and cold viruses. As such, the use of an antiviral agent to treat infection would also prove beneficial, and could include, for example, treatment of influenza and cold viruses, or other transient viruses.

In view of the foregoing, a synthetic lysine analog or mimetic would be beneficial in treatment of viruses like the herpes viruses, inhibiting the recurrence of outbreaks of viruses like the herpes viruses, inhibiting the development of viruses like HIV, and avoiding or treating infection by viruses like influenza and cold viruses, or other transient viruses, where the lysine analog or mimetic either mimics and enhances the effect of lysine in antagonizing other amino acids required for viral replication, or competes with, and blocks, natural lysine when it is needed for viral replication. In addition, because an antiviral synthetic lysine analog or mimetic acts at the fundamental level of the amino acids, the basic building blocks of all proteins and certain other metabolic activities, it is much less likely to be susceptible to viral resistance (e.g., mutation around the activity of the agent) than the usual antiviral drugs that act upon a particular protein or its actions.

The current disclosure herein seeks to utilize the pharmacology of synthetic analogs or mimetics of lysine to antagonize amino acids that are required for certain viruses to replicate, or to compete with natural lysine when it is needed by a virus to replicate. The present disclosure includes methods and compositions to minimize the severity and duration of herpes virus outbreaks and treat infection by certain viruses that are frequently transmitted, such as cold and influenza viruses, or other transient viruses, using synthetic lysine analogs or mimetics. Furthermore, the current disclosure includes methods and compositions for prophylactic use of synthetic lysine analogs or mimetics for the prevention or reduced incidence of outbreaks of viruses that remain chronically in the human body, such as HSV-1 and HSV-2, which are involved in cold sore and genital herpes outbreaks, inhibiting the development and growth of viruses that remain chronically in the human body and continue to replicate and develop over time with increasingly negative consequences, such as HIV, and prevention of infection by certain viruses that are frequently transmitted, such as cold and influenza viruses, or other transient viruses.

Based on studies and research showing that the amino acid lysine is important for the replication of certain viruses, and that supplemental lysine may antagonize or block the activity of other amino acids required for the replication of certain viruses, as well as knowledge of how synthetic lysine analogs or mimetics may in some instances mimic and, in other instances compete with natural lysine, the present disclosure includes methods and compositions for using synthetic lysine analogs or mimetics chronically or prophylactically to inhibit viral replication and thereby reduce the incidence of recurrent outbreaks of certain viruses, like HSV-1 and HSV-2, to suppress the development of other chronic viruses, like HIV, and to avoid infection by certain viruses, such as influenza and cold viruses, or other transient viruses.

In some embodiments, the synthetic lysine analog can be tranexamic acid. In various embodiments, the synthetic lysine analog can be epsilon-aminocaproic acid (EACA). In other embodiments, different agents can be utilized that are lysine-mimetics, for example, AZD 6564, or any other compound that imitates or mimics the function of lysine by treating, preventing, or reducing viral outbreaks, suppressing development or growth of chronic viral infections, or preventing or treating viral infections in the same manner as synthetic lysine analogs, such as tranexamic acid.

Laboratory tests, described below in more detail, indicate that at least one synthetic lysine analog, tranexamic acid, is effective in inhibiting the replication of HSV-1 and HSV-2. In addition, as described in detail further below, laboratory tests indicate that adding tranexamic acid to cells infected with HIV inhibited the replication of the virus. Thus, in the case of this virus, tranexamic acid apparently competes with natural lysine, that is, it blocks lysine from its usual use by the viral replication mechanism, which is similar to tranexamic acid's antifibrinolytic effect, in which it competes with natural lysine by occupying the usual binding locations on plasminogen and thereby keeps the plasminogen from converting to plasmin.

Additionally, laboratory tests indicate tranexamic acid is effective in inhibiting the replication of the Influenza A virus (H3N2), demonstrating tranexamic acid's distinct antiviral performance. Moreover, further laboratory tests indicate that excess amounts of one of the three basic amino acids (lysine, arginine, histidine, or analogs or mimetics thereof) will interfere in the activity of the other two, and an excess amount of a combination of two of them will have the same effect on the third, and further allow a larger dose of the combination without cytotoxicity. As will be discussed in more detail below, adding arginine and tranexamic acid at levels just below cytotoxicity provides the highest level of viral inhibition in the herpes viruses, whereas adding the same amount of tranexamic acid alone produced substantially less inhibition, and adding the same amount of arginine alone increased viral replication.

While studies have shown lysine antagonizes arginine, previous research has indicated that histidine is an important amino acid involved in herpes replication. Based on this research and observed laboratory results, it is contemplated that an overabundance of one basic (non-acidic) amino acid of the three basic amino acids, or analogs or mimetics thereof, might antagonize the other two basic amino acids. Moreover, it is further contemplated that an overabundance of two basic amino acids, or analogs or memetics thereof, will antagonize the third basic amino acid. Laboratory results, discussed below, indicate that tranexamic acid antagonizes arginine and histidine, while tranexamic acid with arginine antagonizes histidine, and tranexamic acid with histidine antagonizes arginine, given sufficient amounts.

Based on the laboratory tests, discussed in detail below, and the studies and research presented above, an objective of the present disclosure is to provide methods and compositions to minimize the severity and duration of a herpes virus outbreak. In accordance with the present disclosure, a therapeutically safe and effective amount of a synthetic lysine analog or mimetic is made available to the infected area as soon as the first signs of an outbreak are noticed and continued until the outbreak has suitably subsided, for example, from 1 to 14 days.

Another objective of the present disclosure is to provide methods and compositions for the prevention of viral outbreaks, such as the occurrence of RHL (cold sores). In accordance with the present disclosure, a therapeutically safe and effective amount of a synthetic lysine analog or mimetic can be made available for prophylactic use, to be administered on a recurrent basis.

It is contemplated that both treatment and prophylactic use could be practiced with systemic administration of the agent, for example, orally, but could also be applied in a topical form in effective concentrations and regimens. In a particular variation of the present disclosure, the synthetic lysine analog includes tranexamic acid, which has been specifically shown to antagonize arginine and histidine and suppress the replication of the HSV-1 and HSV-2 viruses. In another variation of the present disclosure, the synthetic lysine analog includes tranexamic acid with arginine, which has been specifically shown to antagonize histidine and suppress the replication of the HSV-1 and HSV-2 viruses. In some embodiments, the composition, and method of use thereof, can include a synthetic lysine analog or mimetic with one or more amino acid for the treatment, prevention, or reduction of recurring viral outbreaks, such as the herpes viruses, for suppression of development or growth of chronic viral infections, such as HIV, or for prevention or treatment of viral infections, such as the influenza and cold viruses, or other transient viruses.

It is further contemplated that synthetic lysine analogs and mimetics can be utilized to inhibit replication of viruses that remain chronically in the body and continue to develop over time, such as HIV. As such, another objective of the present disclosure is to provide a therapeutically safe and effective amount of a synthetic lysine analog or mimetic that can be made available for prophylactic use, to be administered on a recurrent basis, to suppress the replication and development of the HIV virus. Though varying from the mechanism of inhibiting HSV-1 and HSV-2, it is contemplated that rather than antagonizing arginine and histidine needed by HSV-1 and HSV-2 for replication, tranexamic acid competes with, and displaces, the natural lysine needed by HIV to replicate, similar to how tranexamic acid keeps plasminogen from activating to plasmin (e.g., by occupying the lysine binding sites on plasminogen).

It is further contemplated that synthetic lysine analogs or mimetics can be utilized to avoid or reduce the severity of infection by certain viruses, such as influenza and cold viruses, or other transient viruses, by administering the agent to individuals, for example, who have increased exposure to infection or are at increased risk of serious consequences from infection. Additionally, it is contemplated that synthetic lysine analogs or mimetics can be used to treat infection by certain viruses, such as influenza and cold viruses, or other transient viruses. It is understood that all of these uses of synthetic lysine analogs or mimetics could be used in conjunction with other antiviral remedies when appropriate.

Moreover, due to the inhibiting nature to viruses like the herpes viruses by synthetic lysine analogs or mimetics, it is further envisioned that synthetic lysine analogs or mimetics could be used to facilitate in the prevention of, decrease in progression of, and possible treatment (or used in conjunction with other treatments) for, Alzheimer's disease. Recent studies suggest that two extremely common herpes viruses affect the behavior of genes involved in Alzheimer's disease. Evidence suggests that the brain aggressively defends itself against viruses or other germs, and experiments show that sticky beta-amyloid captures invading germs by engulfing them, which is why plaque starts forming. One of the hallmarks of Alzheimer's disease is the accumulation of amyloid plaques between neurons in the brain. Amyloid is a general term for protein fragments that the body produces normally. Beta amyloid is a protein fragment snipped from an amyloid precursor protein. In a healthy brain, these protein fragments are broken down and eliminated, however, in Alzheimer's disease, the fragments accumulate to form hard, insoluble plaques. In a particular experiment, it was demonstrated that amyloid plaque forms more readily in the absence of a molecule that herpes, in this case, human herpesvirus 6A (HHV6a) and human herpesvirus 7 (HHV7), depletes. This indicates a viral connection exists with Alzheimer's disease. Moreover, it is believed that HHV6 and cold sore-causing herpes viruses can trigger, or seed, amyloid plaque formation. As such, the methods and compositions presented herein for the treatment and suppression of recurrent herpes outbreaks could prove beneficial as a potential prevention or treatment or to slow the progression of Alzheimer's disease. It is understood that these uses of synthetic lysine analogs or mimetics could be used in conjunction with other regimens and treatments of Alzheimer's disease when appropriate.

Viral inhibition by an amino acid that is normally required for the uninfected cell in culture is not unusual. For example, lysine has also been shown to inhibit the GD VII mouse encephalomyelitis virus. Glycine has been found to inhibit poliovirus replication in monkey kidney cells in which glycine is a necessary amino acid. Similarly, glutamine is required for continuing viral replication of the herpes virus, but under certain conditions, glutamine actually effected a reduction in virus yield. Other research found that adding arginine in sufficient amounts and in certain conditions inhibits HSV-1. Arginine also inhibited influenza virus A (H3N2) and poliovirus type 1. As such, the addition of arginine, glutamine, or other amino acids to compositions with tranexamic acid, or other synthetic lysine analog or mimetic agents, is believed to assist in the treatment, prevention, or reduction of one-time or recurring viral outbreaks, such as the herpes viruses, the suppression of development or growth of chronic viral infections, such as HIV, or the prevention or treatment of viral infections, such as the influenza and cold viruses, or other transient viruses.

Reference will now be made to more specific embodiments of the present disclosure and data that provides support for such embodiments. However, it should be noted that the disclosure below is for illustrative purposes only and is not intended to limit the scope of the claimed subject matter in any way.

An embodiment of the present disclosure is directed to the application of synthetic lysine analogs or mimetics to provide for rapid healing and a return to normal cosmetic appearance by utilizing the pharmacologic activity of the agent/composition and its effects on the visible outbreak. The synthetic lysine analogs or mimetics may be in the form of a simple aqueous solution, a solution with inert excipients, or combined with vehicles such as a gel, cream, or lotion, which may optionally contain other treatment ingredients. An additional embodiment to improve handling or treatment delivery, such as via viscous solutions or solutions designed to delay or slowly/predictably deliver the synthetic lysine analog or mimetic are anticipated and would be known by a person of ordinary skill in the art. The solution/composition can be directly administered to the skin area that is showing signs of an outbreak, and can be easy to apply and would adapt easily to the affected area. In some embodiments, the composition utilizes the activity of the agent/composition at the first sign of viral outbreak to reduce the severity and duration of the outbreak and promote a rapid healing process.

In certain embodiments, a synthetic lysine analog or mimetic agent treatment could be practiced with systemic administration of the agent, for example, up to 4 grams per day for 7 days, but could additionally be applied in a topical form in effective concentrations and regimens, for example, a 3 to 5% (w/v) concentration of the agent in 0.25 to 5 mL volumes applied 2 to 3 times per day, in order to provide rapid activity and benefits. In some embodiments, the concentration of the agent can be, for example, up to 30% (w/v) concentration. In various embodiments, the lysine analog or mimetic can antagonize arginine and histidine and suppress the replication of the HSV-1 virus, maintain the amount of natural lysine in the area because it is not able to bind with plasminogen to create plasmin, which otherwise occurs in connection with a trauma to tissues, and block the formation of plasmin and other serine proteases thereby providing anti-inflammatory effects and avoiding the degradation of collagen and the collagen matrix.

Further, an embodiment of the present disclosure is directed to the application of synthetic lysine analogs or mimetic agents to provide the prevention of viral outbreaks by utilizing the pharmacologic activity of the agent/composition. The agent may be a simple aqueous solution, a solution with inert excipients, or combined with vehicles such as a gel, cream, or lotion which may optionally contain other treatment ingredients. Additional embodiments to improve handling and/or prophylactic delivery, such as via viscous solutions or solutions designed to delay, or predictably deliver the synthetic lysine analog or mimetic agents, are also anticipated and would be known by a person of ordinary skill in the art. The solution and/or composition can be directly administered to an area of skin where outbreaks have been known to occur, and can be easy to apply and would adapt easily to the desired area of application. In some embodiments, the solution and/or composition can be a 3 to 10% (w/v) concentration of the synthetic lysine analog or mimetic, or up to 30% (w/v) of the synthetic lysine analog or mimetic.

In some embodiments, the compositions can be used for the prevention or treatment of infections and diseases caused by other viruses including, but not limited to, common cold and influenza viruses, or other transient viruses, for example in persons at increased risk of exposure, or who have been exposed to infection by such viruses but do not yet exhibit symptoms of infection, or persons for whom infection by such viruses could represent a life-threatening event. As several of these viruses attach to the back of the throat and nasal passages, in some embodiments, the compositions can be formulated into sprays, mists, aerosols, and mouth washes, or solutions to be swabbed, that can be applied to mouth, nose and/or throat areas, including the nasal passages. In some embodiments, the solution and/or composition can be a 3 to 10% (w/v) concentration of the synthetic lysine analog or mimetic, or up to 30% (w/v) of the synthetic lysine analog or mimetic.

In other embodiments, the compositions, presented herein, can be utilized for the prevention of viral outbreaks or suppression of the development of viral infections, and can be administered via enteral and parenteral methods, for example, pills, tablets, capsules, or injections. In further embodiments, the compositions can be administered via an injected or implanted liposomal delivery depot for long term administration. In some embodiments, the compositions can be in the form of a transdermal patch that administers the drug via skin contact.

Additionally, some embodiments of the present disclosure are directed to compositions and methods of use thereof, of synthetic lysine analog or mimetic agents in combination with arginine to assist in the treatment and prevention of viral outbreaks, such as the herpes viruses, suppress the development of other chronic viruses, such as HIV, and to avoid or treat infection by certain viruses, for example, influenza and cold viruses, or other transient viruses, by utilizing the pharmacologic activity of excess amount of a combination of lysine analog or mimetic and arginine. In some embodiments, other amino acids that are required to build the proteins needed for viral replication can be used in conjunction with synthetic lysine analogs or mimetics, such as, tranexamic acid, to improve antiviral performance of the synthetic lysine analogs or mimetics.

Moreover, various embodiments of the present disclosure are directed to compositions and methods of use thereof, of synthetic lysine analog or mimetic agents in combination with one or more amino acids, for example, a synthetic lysine analog such as tranexamic acid with lysine, arginine, or histidine, for the treatment and prevention of viral outbreaks, such as the herpes viruses, suppression of the development of other chronic viruses, such as HIV, and to avoid or treat infection by certain viruses, for example, influenza and cold viruses, or other transient viruses. In various embodiments, the synthetic lysine analog or mimetic can be used in conjunction with one or more synthetic amino acids, analogs, or mimetics thereof, for the treatment and prevention of viral outbreaks, suppression of the development of other chronic viruses, such as HIV, and to avoid or treat infection by certain viruses, for example, influenza and cold viruses, or other transient viruses.

In some embodiments, the synthetic lysine analogs or mimetics can be in combination with one or more of any amino acid (e.g., aliphatic, aromatic, acidic, basic, neutral, or unique amino acids) or combinations thereof, for the treatment and prevention of viral outbreaks, such as the herpes viruses, suppression of the development of other chronic viruses, such as HIV, and to avoid or treat infection by certain viruses, for example, influenza and cold viruses, or other transient viruses.

In various embodiments the present disclosure is directed to compositions, and methods of use thereof, of synthetic lysine analog or mimetic agents in combination with glutamine for the treatment, prevention, or reduction of recurring viral outbreaks, such as the herpes viruses, for suppression of development or growth of chronic viral infections, such as HIV, or for prevention or treatment of viral infections, such as the influenza and cold viruses, or other transient viruses. In a particular embodiment, the composition can include tranexamic acid and glutamine. In other embodiments, the composition can include tranexamic acid, glutamine, and one or more amino acids, such as, lysine, arginine, or histidine.

Antiviral Activity of Tranexamic Acid

The evaluation of antiviral activity, namely the reduction of viral replication, of tranexamic acid was conducted for HSV-1, HSV-2, HIV, and Influenza A Virus (H3N2). Each evaluation consisted of a high and low virus inocula with an input virus control (no tranexamic acid) used for the input viral titer in determining the $Log_{10}$ reduction and the corresponding replication reduction percentage.

Additionally, the evaluation of antiviral activity of 2% (w/v) tranexamic acid, L-arginine (with varying concentrations), and a mixture of 2% (w/v) tranexamic acid and L-arginine (with varying concentrations) was conducted for HSV-1 and HSV-2 to demonstrate the effects of the combination of tranexamic acid and L-arginine on viral reduction percentage and to identify how tranexamic acid inhibits HSV-1 and HSV-2 replication. Each evaluation consisted of an input virus control (no extraneous tranexamic acid or L-arginine) used for the input viral titer in determining replication reduction percentage.

As will be discussed in further detail below, tranexamic acid at 0.5% (w/v), 1.0% (w/v), and 2.0% (w/v) were used in the evaluation of HSV-1 and HSV-2 replication reduction, while tranexamic acid at 2.0% (w/v), 3.0% (w/v), and 4.0% (w/v) were used in the evaluation of HIV replication reduction based on the cytotoxicity limitations of the cell media for the two different types of virus. Tranexamic acid at 6% (w/v), 8% (w/v), and 10% (w/v) were used in the evaluation of H3N2 replication reduction.

As will be illustrated in further detail below, L-arginine at 5,000 μM, 10,000 μM, and 25,000 μM, with HSV-1 and HSV-2 was evaluated and contrasted to the evaluation of 2% (w/v) tranexamic acid with 5,000 μM L-arginine, 2% (w/v) tranexamic acid with 10,000 μM L-arginine, and 2% (w/v) tranexamic acid with 25,000 μM L-arginine, with HSV-1 and HSV-2 to demonstrate the underlying mechanism of action of tranexamic acid in inhibiting HSV-1 and HSV-2 replication and show the increased effect of viral reduction percentages with combination mixtures of tranexamic acid and L-arginine.

Further illustrated in detail below, L-arginine at varying concentrations, L-histidine at varying concentrations, 2% (w/v) tranexamic acid with L-arginine at various concentrations, 2% (w/v) tranexamic acid with L-histidine at various concentrations, and 2% (w/v) tranexamic acid with varying concentrations of L-arginine and L-histidine, were evaluated with HSV-1 to confirm that tranexamic acid antagonizes arginine and histidine, while mixtures of tranexamic acid with arginine antagonize histidine, and mixtures of tranexamic acid with histidine antagonize arginine, at sufficient amounts. In essence, as shown below, the addition of one or more amino acids to tranexamic acid can significantly improve the effectiveness of antiviral activity. This improved effectiveness is accomplished by the overabundance of amino acids antagonizing the other amino acid (e.g., tranexamic acid, acting as lysine, in combination with arginine antagonizes histidine).

Antiviral Activity of Tranexamic Acid Against Herpes Simplex Virus Type 1 (HSV-1)

Each sample tested and shown below each had 3 replicates and consisted of an input virus control at 0% (w/v) tranexamic acid, tranexamic acid at 0.5% (w/v), 1.0% (w/v), and 2.0% (w/v) for low and high virus inocula. Contact time for each sample was 48±8 hours and reduction factors were generated using input viral titer ($Log_{10}TCID_{50}$) and output viral titer ($Log_{10}TCID_{50}$) resulting in $Log_{10}$ reduction factors with the correlating reduction percentage.

Preparation for evaluation of antiviral activity of tranexamic acid against HSV-1, for low virus inocula, was prepared as follows: 0.25 mL of virus inoculum (containing $10^{6.26}$ $TCID_{50}$ units) was added to 3 wells for each dose of tranexamic acid or input virus control. The inocula was incubated for 90 minutes at 36±2° C. with 5±3% $CO_2$. The inoculum was removed and the wells washed three times with PBS. 1.0 mL of each dose of tranexamic acid (or DM for input virus control) was added to each well. The plate was incubated for 48±8 hours at 36±2° C. with 5±3% $CO_2$. The plate was then frozen at -60 to -90° C. overnight, thawed, and the contents of each well centrifuged at 2,000 RPM for 10 minutes. The supernatant from each well was collected and assayed for infectious virus.

Titer results are depicted in Table 1 below, the input virus control titer ($Log_{10}TCID_{50}/mL$) for the low virus inocula ranged from 5.95±0.10 to 6.55±0.10 with an average of 6.26±0.10, with the virus stock titer control having a titer of 2.30±0.19. Sample amounts of tranexamic acid at 0.5% (w/v), 1.0% (w/v), and 2.0% (w/v) having titer values ($Log_{10}TCID_{50}/mL$) as indicated below, were used in the testing.

TABLE 1

| Sample | Virus Inocula | Replicate Number | Contact Time | Titer ($Log_{10}TCID_{50}/mL$) |
|---|---|---|---|---|
| Cell viability/media sterility control | NA | NA | NA | no virus was detected, cells were viable; media sterile |
| Virus Stock Titer Control | Low | | | 2.30 ± 0.19 |
| Input Virus Control (0% Tranexamic Acid) | Low | 1 | 48 ± 8 hours | 6.55 ± 0.10 |
| | | 2 | | 6.01 ± 0.11 |
| | | 3 | | 5.95 ± 0.10 |
| | Input Virus Control (Low) - Average | | | 6.26 ± 0.10 |
| Tranexamic Acid - 0.5% | Low | 1 | 48 ± 8 hours | 5.83 ± 0.00 |
| | | 2 | | 5.24 ± 0.10 |
| | | 3 | | 5.54 ± 0.09 |
| Tranexamic Acid - 1.0% | Low | 1 | | 5.65 ± 0.09 |
| | | 2 | | 4.58 ± 0.12 |
| | | 3 | | 4.34 ± 0.10 |
| Tranexamic Acid - 2.0% | Low | 1 | | 4.76 ± 0.08 |
| | | 2 | | 3.69 ± 0.10 |
| | | 3 | | 4.04 ± 0.08 |

Preparation for evaluation of antiviral activity of tranexamic acid against HSV-1, for high virus inocula, was prepared as follows: 0.25 mL of virus inoculum (containing $10^{6.46}$ $TCID_{50}$ units) was added to 3 wells for each dose of tranexamic acid or input virus control. The inocula was incubated for 90 minutes at 36±2° C. with 5±3% $CO_2$. The inoculum was removed and the wells washed three times with PBS. 1.0 mL of each dose of tranexamic acid (or DM for input virus control) was added to each well. The plate was incubated for 48±8 hours at 36±2° C. with 5±3% $CO_2$. The plate was then frozen at -60 to -90° C. overnight, thawed, and the contents of each well centrifuged at 2,000 RPM for 10 minutes. The supernatant from each well was collected and assayed for infectious virus.

Titer results are depicted in Table 2 below, the input virus control titer ($Log_{10}TCID_{50}/mL$) for the high virus inocula ranged from 6.37±0.13 to 6.55±0.14 with an average of 6.46±0.13, with the virus stock titer control having a titer of 2.30±0.19. Sample amounts of tranexamic acid at 0.5% (w/v), 1.0% (w/v), and 2.0% (w/v) having titer values ($Log_{10}TCID_{50}/mL$) as indicated below, were used in the testing.

TABLE 2

| Sample | Virus Inocula | Replicate Number | Contact Time | Titer ($Log_{10}TCID_{50}/mL$) |
|---|---|---|---|---|
| Cell viability/media sterility control | NA | NA | NA | no virus was detected, cells were viable; media sterile |

TABLE 2-continued

| Sample | Virus Inocula | Replicate Number | Contact Time | Titer ($Log_{10}TCID_{50}$/mL) |
|---|---|---|---|---|
| Virus Stock Titer Control | High | | | 2.30 ± 0.19 |
| Input Virus Control | High | 1 | 48 ± 8 | 6.37 ± 0.13 |
| (0% Tranexamic Acid) | | 2 | hours | 6.43 ± 0.12 |
| | | 3 | | 6.55 ± 0.14 |
| | Input Virus Control (High) - Average | | | 6.46 ± 0.13 |
| Tranexamic Acid - 0.5% | High | 1 | 48 ± 8 | 6.19 ± 0.08 |
| | | 2 | hours | 6.43 ± 0.13 |
| | | 3 | | 6.37 ± 0.11 |
| Tranexamic Acid - 1.0% | High | 1 | | 6.43 ± 0.12 |
| | | 2 | | 6.61 ± 0.11 |
| | | 3 | | 6.43 ± 0.13 |
| Tranexamic Acid - 2.0% | High | 1 | | 5.71 ± 0.12 |
| | | 2 | | 5.42 ± 0.06 |
| | | 3 | | 5.42 ± 0.06 |

The resulting reduction factors are shown below in Table 3, where the input virus control average was used as the input viral titer. As can be seen in Table 3, the reduction percent peaked at 90.5% for tranexamic acid at 0.5% (w/v), 98.8% for tranexamic acid at 1.0% (w/v), and 99.7% for tranexamic acid at 2.0% (w/v) in the low virus inocula. The data shows higher reduction percentages as the tranexamic acid percentage increases, as would be expected, on the low virus inocula and an increase in reduction percentages was observed between tranexamic acid percentages of 0.5% (w/v) and 2.0% (w/v) on the high virus inocula. The reduction percent peaked at 45.9% for tranexamic acid at 0.5% (w/v), 5.9% for tranexamic acid at 1.0% (w/v), and 90.8% for tranexamic acid at 2.0% (w/v) in the high virus inocula. Particular attention should be noted on the percent reduction of the tranexamic acid at 2.0% (w/v), especially as indicated in the low virus inocula which demonstrated a greater than 99% reduction. Prior to an outbreak, the level of viral infection would be relatively low, so the effectiveness of tranexamic acid at this level is more relevant to the suppression of an outbreak.

TABLE 3

| Test Article | Virus Inocula | Replicate Number | Contact Time | Input Viral Titer ($Log_{10}TCID_{50}$) | Output Viral Titer ($Log_{10}TCID_{50}$) | $Log_{10}$ Reduction | Reduction (%) |
|---|---|---|---|---|---|---|---|
| Tranexamic | Low | 1 | 48 ± 8 | 6.26 | 5.83 | 0.43 | 62.9 |
| Acid-0.5% | | 2 | hours | 6.26 | 5.24 | 1.02 | 90.5 |
| | | 3 | | 6.26 | 5.54 | 0.72 | 81.0 |
| Tranexamic | | 1 | | 6.26 | 5.65 | 0.61 | 75.5 |
| Acid-1.0% | | 2 | | 6.26 | 4.58 | 1.68 | 97.9 |
| | | 3 | | 6.26 | 4.34 | 1.92 | 98.8 |
| Tranexamic | | 1 | | 6.26 | 4.76 | 1.50 | 96.8 |
| Acid-2.0% | | 2 | | 6.26 | 3.69 | 2.57 | 99.7 |
| | | 3 | | 6.26 | 4.04 | 2.22 | 99.4 |
| Tranexamic | High | 1 | 48 ± 8 | 6.46 | 6.19 | 0.27 | 45.9 |
| Acid-0.5% | | 2 | hours | 6.46 | 6.43 | 0.03 | 5.9 |
| | | 3 | | 6.46 | 6.37 | 0.09 | 18.1 |
| Tranexamic | | 1 | | 6.46 | 6.43 | 0.03 | 5.9 |
| Acid-1.0% | | 2 | | 6.46 | 6.61 | −0.15 | No reduction |
| | | 3 | | 6.46 | 6.43 | 0.03 | 5.9 |
| Tranexamic | | 1 | | 6.46 | 5.71 | 0.75 | 82.1 |
| Acid-2.0% | | 2 | | 6.46 | 5.42 | 1.04 | 90.8 |
| | | 3 | | 6.46 | 5.42 | 1.04 | 90.8 |

Antiviral Activity of Tranexamic Acid Against Herpes Simplex Virus Type 2 (HSV-2)

Each sample tested and shown below each had 3 replicates and consisted of an input virus control at 0% (w/v) tranexamic acid, tranexamic acid at 0.5% (w/v), 1.0% (w/v), and 2.0% (w/v) for low and high virus inocula. Contact time for each sample was 48±8 hours and reduction factors were generated using input viral titer ($Log_{10}TCID_{50}$) and output viral titer ($Log_{10}TCID_{50}$) resulting in $Log_{10}$ reduction factors with the correlating reduction percentage.

Preparation for evaluation of antiviral activity of tranexamic acid against HSV-2, for low virus inocula, was prepared as follows: 0.25 mL of virus inoculum (containing $10^{2.1}$ $TCID_{50}$ units) was added to 3 wells for each dose of tranexamic acid or input virus control. The inocula was incubated for 90 minutes at 36±2° C. with 5±3% $CO_2$. The inoculum was removed and the wells washed three times with PBS. 1.0 mL of each dose of tranexamic acid (or DM for input virus control) was added to each well. The plate was incubated for 48±8 hours at 36±2° C. with 5±3% $CO_2$. The plate was then frozen at −60 to −90° C. for 6 days, thawed, and the contents of each well centrifuged at 2,000 RPM for 10 minutes. The supernatant from each well was collected and assayed for infectious virus.

Titer results are depicted in Table 4 below, the input virus control titer ($Log_{10}TCID_{50}$/mL) for the low virus inocula ranged from 6.13±0.09 to 6.31±0.08 with an average of 6.22±0.08, with the virus stock titer control having a titer of 2.68±0.20. Sample amounts of tranexamic acid at 0.5% (w/v), 1.0% (w/v), and 2.0% having titer values ($Log_{10}TCID_{50}$/mL) as indicated below, were used in the testing.

ranged from 7.74±0.11 to 7.92±0.09 with an average of 7.83±0.09, with the virus stock titer control having a titer of 4.43±0.18. Sample amounts of tranexamic acid at 0.5% (w/v), 1.0% (w/v), and 2.0% (w/v), having titer values ($Log_{10}TCID_{50}$/mL) as indicated below, were used in the testing.

TABLE 4

| Sample | Virus Inocula | Replicate Number | Contact Time | Titer ($Log_{10}TCID_{50}$/mL) |
|---|---|---|---|---|
| Cell viability/media sterility control | NA | NA | NA | no virus was detected, cells were viable; media sterile |
| Virus Stock Titer Control | Low | | | 2.68 ± 0.20 |
| Input Virus Control (0% Tranexamic Acid) | Low | 1 | 48 ± 8 hours | 6.31 ± 0.08 |
| | | 2 | | 6.19 ± 0.08 |
| | | 3 | | 6.13 ± 0.09 |
| Input Virus Control (Low) - Average | | | | 6.22 ± 0.08 |
| Tranexamic Acid - 0.5% | Low | 1 | 48 ± 8 hours | 5.54 ± 0.09 |
| | | 2 | | 5.77 ± 0.10 |
| | | 3 | | 5.71 ± 0.08 |
| Tranexamic Acid - 1.0% | Low | 1 | | 5.89 ± 0.10 |
| | | 2 | | 5.60 ± 0.09 |
| | | 3 | | 5.83 ± 0.08 |
| Tranexamic Acid - 2.0% | Low | 1 | | 4.76 ± 0.10 |
| | | 2 | | 4.34 ± 0.12 |
| | | 3 | | 4.40 ± 0.11 |

Preparation for evaluation of antiviral activity of tranexamic acid against HSV-2, for high virus inocula, was prepared as follows: 0.25 mL of virus inoculum (containing $10^{3.8}$ $TCID_{50}$ units) was added to 3 wells for each dose of tranexamic acid or input virus control. The inocula was incubated for 90 minutes at 36±2° C. with 5±3% $CO_2$. The inoculum was removed and the wells washed three times with PBS. 1.0 mL of each dose of tranexamic acid (or DM for input virus control) was added to each well. The plate was incubated for 48±8 hours at 36±2° C. with 5±3% $CO_2$. The plate was then frozen at −60 to −90° C. for 6 days, thawed, and the contents of each well centrifuged at 2,000 RPM for 10 minutes. The supernatant from each well was collected and assayed for infectious virus.

Titer results are depicted in Table 5 below, the input virus control titer ($Log_{10}TCID_{50}$/mL) for the high virus inocula

TABLE 5

| Sample | Virus Inocula | Replicate Number | Contact Time | Titer ($Log_{10}TCID_{50}$/mL) |
|---|---|---|---|---|
| Cell viability/media sterility control | NA | NA | NA | no virus was detected, cells were viable; media sterile |
| Virus Stock Titer Control | High | | | 4.43 ± 0.18 |
| Input Virus Control (0% Tranexamic Acid) | High | 1 | 48 ± 8 hours | 7.80 ± 0.06 |
| | | 2 | | 7.92 ± 0.09 |
| | | 3 | | 7.74 ± 0.11 |
| Input Virus Control (High) - Average | | | | 7.83 ± 0.09 |
| Tranexamic Acid - 0.5% | High | 1 | 48 ± 8 hours | 7.50 ± 0.09 |
| | | 2 | | 7.86 ± 0.10 |
| | | 3 | | 7.56 ± 0.09 |
| Tranexamic Acid - 1.0% | High | 1 | | 7.62 ± 0.08 |
| | | 2 | | 7.44 ± 0.11 |
| | | 3 | | 7.38 ± 0.10 |
| Tranexamic Acid - 2.0% | High | 1 | | 4.04 ± 0.08 |
| | | 2 | | 4.10 ± 0.09 |
| | | 3 | | 5.00 ± 0.10 |

The resulting reduction factors are shown below in Table 6, where the input virus control average was used as the input viral titer. As can be seen in Table 6, the reduction percent peaked at 78.94% for tranexamic acid at 0.5% (w/v), 75.82% for tranexamic acid at 1.0% (w/v), and 98.67% for tranexamic acid at 2.0% (w/v) in the low virus inocula. The data shows higher reduction percentages of the tranexamic acid at 2.0% (w/v) on the low virus inocula and a general increase in reduction percentages as the tranexamic acid percentage increases on the high virus inocula. The reduction percent peaked at 52.85% for tranexamic acid at 0.5% (w/v), 64.24% for tranexamic acid at 1.0% (w/v), and 99.98% for tranexamic acid at 2.0% (w/v) in the high virus inocula. Particular attention should be noted on the percent reduction of the tranexamic acid at 2.0% (w/v), especially as indicated in both the low and high virus inocula, where a reduction greater than 98% is demonstrated.

TABLE 6

| Test Article | Virus Inocula | Replicate Number | Contact Time | Input Viral Titer ($Log_{10}TCID_{50}$) | Output Viral Titer ($Log_{10}TCID_{50}$) | $Log_{10}$ Reduction | Reduction (%) |
|---|---|---|---|---|---|---|---|
| Tranexamic Acid-0.5% | Low | 1 | 48 ± 8 hours | 6.22 | 5.54 | 0.68 | 78.94 |
|  |  | 2 |  | 6.22 | 5.77 | 0.45 | 64.24 |
|  |  | 3 |  | 6.22 | 5.71 | 0.51 | 68.85 |
| Tranexamic Acid-1.0% |  | 1 |  | 6.22 | 5.89 | 0.33 | 52.85 |
|  |  | 2 |  | 6.22 | 5.60 | 0.62 | 75.82 |
|  |  | 3 |  | 6.22 | 5.83 | 0.39 | 58.94 |
| Tranexamic Acid-2.0% |  | 1 |  | 6.22 | 4.76 | 1.46 | 96.51 |
|  |  | 2 |  | 6.22 | 4.34 | 1.88 | 98.67 |
|  |  | 3 |  | 6.22 | 4.40 | 1.82 | 98.47 |
| Tranexamic Acid-0.5% | High | 1 | 48 ± 8 hours | 7.83 | 7.50 | 0.33 | 52.85 |
|  |  | 2 |  | 7.83 | 7.86 | No reduction | No reduction |
|  |  | 3 |  | 7.83 | 7.56 | 0.27 | 45.87 |
| Tranexamic Acid-1.0% |  | 1 |  | 7.83 | 7.62 | 0.21 | 37.85 |
|  |  | 2 |  | 7.83 | 7.44 | 0.39 | 58.94 |
|  |  | 3 |  | 7.83 | 7.38 | 0.45 | 64.24 |
| Tranexamic Acid-2.0% |  | 1 |  | 7.83 | 4.04 | 3.79 | 99.98 |
|  |  | 2 |  | 7.83 | 4.10 | 3.73 | 99.98 |
|  |  | 3 |  | 7.83 | 5.00 | 2.83 | 99.85 |

Antiviral Activity of Tranexamic Acid Against Human Immunodeficiency Virus Type 1 (HIV-1)

Each sample tested and shown below each had 3 replicates and consisted of an input virus control at 0% (w/v) tranexamic acid, tranexamic acid at 2.0% (w/v), 3.0% (w/v), and 4.0% (w/v) for low and high virus inocula. Contact time for each sample was 48±8 hours and reduction factors were generated using input viral titer ($Log_{10}TCID_{50}$) and output viral titer ($Log_{10}TCID_{50}$) resulting in $Log_{10}$ reduction factors with the correlating reduction percentage.

Preparation for evaluation of antiviral activity of tranexamic acid against HIV-1, for low virus inocula, was prepared as follows: 0.5 mL of virus inoculum (containing $10^{2.0}$ $TCID_{50}$ units) was added to 3 wells for each dose of tranexamic acid or input virus control. 1.0 mL of each dose of tranexamic acid (or DM for input virus control) was added to each well. The plate was incubated for 48±8 hours at 36±2° C. with 5±3% $CO_2$. The plate was then frozen at −60 to −90° C. for 1 day, thawed, and the contents of each well centrifuged at 2,000 RPM for 10 minutes. The supernatant from each well was collected and assayed for infectious virus.

Titer results are depicted in Table 7 below, the input virus control titer ($Log_{10}TCID_{50}$/mL) for the low virus inocula ranged from 4.34±0.10 to 4.46±0.10 with an average of 4.40±0.08, with the virus stock titer control having a titer of 2.30±0.19. Sample amounts of tranexamic acid at 2.0% (w/v), 3.0% (w/v), and 4.0% (w/v) having titer values ($Log_{10}TCID_{50}$/mL) as indicated below, were used in the testing.

TABLE 7

| Sample | Virus Inocula | Replicate Number | Contact Time | Titer ($Log_{10}TCID_{50}$/mL) |
|---|---|---|---|---|
| Cell viability/media sterility control | NA | NA | NA | no virus was detected, cells were viable; media sterile |
| Virus Stock Titer Control | Low |  |  | 2.30 ± 0.19 |
| Input Virus Control (0% Tranexamic Acid) | Low | 1 | 48 ± 8 hours | 4.34 ± 0.10 |
|  |  | 2 |  | 4.40 ± 0.00 |
|  |  | 3 |  | 4.46 ± 0.10 |
| Input Virus Control (Low) - Average |  |  |  | 4.40 ± 0.08 |
| Tranexamic Acid - 2.0% | Low | 1 | 48 ± 8 hours | 4.22 ± 0.09 |
|  |  | 2 |  | 4.16 ± 0.09 |
|  |  | 3 |  | 4.04 ± 0.08 |
| Tranexamic Acid - 3.0% | Low | 1 |  | 3.93 ± 0.00 |
|  |  | 2 |  | 4.04 ± 0.10 |
|  |  | 3 |  | 4.34 ± 0.10 |
| Tranexamic Acid - 4.0% | Low | 1 |  | 2.79 ± 0.09 |
|  |  | 2 |  | 2.85 ± 0.08 |
|  |  | 3 |  | 2.55 ± 0.06 |

Preparation for evaluation of antiviral activity of tranexamic acid against HIV-1, for high virus inocula, was prepared as follows: 0.5 mL of virus inoculum (containing $10^{3.88}$ $TCID_{50}$ units) was added to 3 wells for each dose of tranexamic acid or input virus control. 1.0 mL of each dose of tranexamic acid (or DM for input virus control) was added to each well. The plate was incubated for 48±8 hours at 36±2° C. with 5±3% $CO_2$. The plate was then frozen at −60 to −90° C. for 1 day, thawed, and the contents of each well centrifuged at 2,000 RPM for 10 minutes. The supernatant from each well was collected and assayed for infectious virus.

Titer results are depicted in Table 8 below, the input virus control titer ($Log_{10}TCID_{50}$/mL) for the high virus inocula ranged from 5.71±0.10 to 6.31±0.08 with an average of 6.06±0.09, with the virus stock titer control having a titer of 4.18±0.18. Sample amounts of tranexamic acid at 2.0% (w/v), 3.0% (w/v), and 4.0% (w/v) having titer values ($Log_{10}TCID_{50}$/mL) as indicated below, were used in the testing.

TABLE 8

| Sample | Virus Inocula | Replicate Number | Contact Time | Titer ($Log_{10}TCID_{50}$/mL) |
|---|---|---|---|---|
| Cell viability/media sterility control | NA | NA | NA | no virus was detected, cells were viable; media sterile |
| Virus Stock Titer Control | High | | | 4.18 ± 0.18 |
| Input Virus Control (0% Tranexamic Acid) | High | 1 | 48 ± 8 hours | 5.71 ± 0.10 |
| | | 2 | | 5.95 ± 0.08 |
| | | 3 | | 6.31 ± 0.08 |
| Input Virus Control (High) - Average | | | | 6.06 ± 0.09 |
| Tranexamic Acid - 2.0% | High | 1 | 48 ± 8 hours | 5.83 ± 0.00 |
| | | 2 | | 6.01 ± 0.09 |
| | | 3 | | 6.01 ± 0.11 |
| Tranexamic Acid - 3.0% | High | 1 | | 5.83 ± 0.00 |
| | | 2 | | 5.71 ± 0.10 |
| | | 3 | | 6.01 ± 0.09 |
| Tranexamic Acid - 4.0% | High | 1 | | 4.82 ± 0.10 |
| | | 2 | | 4.70 ± 0.09 |
| | | 3 | | 4.52 ± 0.08 |

The resulting reduction factors are shown below in Table 9, where the input virus control average was used as the input viral titer. As can be seen in Table 9, the reduction percent peaked at 56.6% for tranexamic acid at 2.0% (w/v), 66.3% for tranexamic acid at 3.0% (w/v), and 98.6% for tranexamic acid at 4.0% (w/v) in the low virus inocula. The data shows higher reduction percentages as the tranexamic acid percentage increases, as would be expected, on the low virus inocula and an increase in reduction percentages as the tranexamic acid percentage increases on the high virus inocula. The reduction percent peaked at 41.1% for tranexamic acid at 2.0% (w/v), 55.3% for tranexamic acid at 3.0% (w/v), and 97.1% for tranexamic acid at 4.0% (w/v) in the high virus inocula. Particular attention should be noted on the percent reduction of the tranexamic acid at 4.0% (w/v), especially as indicated in both the low and high virus inocula, where a reduction greater than 95% is demonstrated.

TABLE 9

| Test Article | Virus Inocula | Replicate Number | Contact Time | Input Viral Titer ($Log_{10}TCID_{50}$) | Output Viral Titer ($Log_{10}TCID_{50}$) | $Log_{10}$ Reduction | Reduction (%) |
|---|---|---|---|---|---|---|---|
| Tranexamic Acid-2.0% | Low | 1 | 48 ± 8 hours | 4.40 | 4.22 | 0.18 | 34.3 |
| | | 2 | | 4.40 | 4.16 | 0.24 | 42.8 |
| | | 3 | | 4.40 | 4.04 | 0.36 | 56.6 |
| Tranexamic Acid-3.0% | | 1 | | 4.40 | 3.93 | 0.47 | 66.3 |
| | | 2 | | 4.40 | 4.04 | 0.36 | 56.6 |
| | | 3 | | 4.40 | 4.34 | 0.06 | 13.5 |
| Tranexamic Acid-4.0% | | 1 | | 4.40 | 2.79 | 1.61 | 97.6 |
| | | 2 | | 4.40 | 2.85 | 1.55 | 97.2 |
| | | 3 | | 4.40 | 2.55 | 1.85 | 98.6 |
| Tranexamic Acid-2.0% | High | 1 | 48 ± 8 hours | 6.06 | 5.83 | 0.23 | 41.1 |
| | | 2 | | 6.06 | 6.01 | 0.05 | 10.9 |
| | | 3 | | 6.06 | 6.01 | 0.05 | 10.9 |

TABLE 9-continued

| Test Article | Virus Inocula | Replicate Number | Contact Time | Input Viral Titer ($Log_{10}TCID_{50}$) | Output Viral Titer ($Log_{10}TCID_{50}$) | $Log_{10}$ Reduction | Reduction (%) |
|---|---|---|---|---|---|---|---|
| Tranexamic Acid-3.0% | | 1 | | 6.06 | 5.83 | 0.23 | 41.1 |
| | | 2 | | 6.06 | 5.71 | 0.35 | 55.3 |
| | | 3 | | 6.06 | 6.01 | 0.05 | 10.9 |
| Tranexamic Acid-4.0% | | 1 | | 6.06 | 4.82 | 1.24 | 94.2 |
| | | 2 | | 6.06 | 4.70 | 1.36 | 95.6 |
| | | 3 | | 6.06 | 4.52 | 1.54 | 97.1 |

Antiviral Activity of Tranexamic Acid Against Influenza a Virus (H3N2) Using Chicken Embryonated Eggs as Infection System Each sample tested and shown below each had 4 replicates and consisted of an input virus control at 0% (w/v) tranexamic acid, tranexamic acid at 6% (w/v), 8% (w/v), and 10% (w/v) for low and high virus inocula. Contact time for each sample was 72±8 hours and reduction factors were generated using input viral titer ($Log_{10}TCID_{50}$) and output viral titer ($Log_{10}TCID_{50}$) resulting in $Log_{10}$ reduction factors with the correlating reduction percentage.

Preparation for evaluation of antiviral activity of tranexamic acid against H3N2, for low virus inocula, was prepared as follows: 0.2 mL of tranexamic acid-virus mixture (containing $10^{3.0}$ $TCID_{50}$/mL) was added to 4 embryonated chicken eggs for each dose of tranexamic acid or input virus control. The eggs were incubated for 72±8 hours at 36±2° C. The eggs were then held at 1 to 10° C. overnight. The allantoic fluid was then harvested and held at −60 to −90° C. until assay, upon which the samples were thawed and centrifuged at 2,000 RPM for 15 minutes. The supernatant from each sample was collected and assayed for infectious virus.

Titer results are depicted in Table 10 below, the input virus control titer ($Log_{10}TCID_{50}$/mL) for the low virus inocula ranged from 7.00±0.28 to 8.00±0.28 with an average of 7.64±0.27, with the virus stock titer control having a titer of 3.50±0.00. Sample amounts of tranexamic acid at 6% (w/v), 8% (w/v), and 10% (w/v) having titer values ($Log_{10}TCID_{50}$/mL) as indicated below, were used in the testing.

TABLE 10

| Sample | Virus Inocula | Replicate Number | Contact Time | Titer ($Log_{10}TCID_{50}$/mL) |
|---|---|---|---|---|
| Cell viability/media sterility control | NA | NA | NA | no virus was detected, cells were viable; media sterile |
| Virus Stock Titer Control | Low | | | 3.50 ± 0.00 |
| Input Virus Control (0% Tranexamic Acid) | Low | 1 | 72 ± 8 hours | 7.00 ± 0.28 |
| | | 2 | | 7.00 ± 0.28 |
| | | 3 | | 7.75 ± 0.25 |
| | | 4 | | 8.00 ± 0.28 |
| Input Virus Control (Low) - Average | | | | 7.64 ± 0.27 |
| 6% Tranexamic Acid | Low | 1 | 72 ± 8 hours | 7.00 ± 0.28 |
| | | 2 | | 6.50 ± 0.00 |
| | | 3 | | 6.75 ± 0.25 |
| | | 4 | | 6.25 ± 0.25 |
| 8% Tranexamic Acid | Low | 1 | | 4.75 ± 0.25 |
| | | 2 | | 4.00 ± 0.28 |
| | | 3 | | 4.25 ± 0.25 |
| | | 4 | | 5.25 ± 0.25 |
| 10% Tranexamic Acid | Low | 1 | | 4.25 ± 0.25 |
| | | 2 | | 3.75 ± 0.25 |
| | | 3 | | 4.25 ± 0.37 |
| | | 4 | | 4.25 ± 0.25 |

Preparation for evaluation of antiviral activity of tranexamic acid against H3N2, for high virus inocula, was prepared as follows: 0.2 mL of tranexamic acid-virus mixture (containing $10^{5.0}$ TCID$_{50}$/mL) was added to 4 embryonated chicken eggs for each dose of tranexamic acid or input virus control. The eggs were incubated for 72±8 hours at 36±2° C. The eggs were then held at 1 to 10° C. overnight. The allantoic fluid was then harvested and held at −60 to −90° C. until assay, upon which the samples were thawed and centrifuged at 2,000 RPM for 15 minutes. The supernatant from each sample was collected and assayed for infectious virus.

Titer results are depicted in Table 11 below, the input virus control titer (Log$_{10}$TCID$_{50}$/mL) for the high virus inocula ranged from 6.00±0.28 to 7.00±0.28 with an average of 6.74±0.28, with the virus stock titer control having a titer of 5.50±0.00. Sample amounts of tranexamic acid at 6% (w/v), 8% (w/v), and 10% (w/v) having titer values (Log$_{10}$TCID$_{50}$/mL) as indicated below, were used in the testing.

and the high virus inocula was $10^{5.0}$ TCID$_{50}$/mL. As can be seen in Table 12, the reduction percent peaked at 95.96% for tranexamic acid at 6% (w/v), 99.98% for tranexamic acid at 8% (w/v), and 99.99% for tranexamic acid at 10% (w/v) in the low virus inocula. The data shows higher reduction percentages as the tranexamic acid percentage increases, as would be expected, on the low virus inocula and an increase in reduction percentages as the tranexamic acid percentage increases on the high virus inocula, though three out of the four replicates showed no viral reduction for tranexamic acid at 6% (w/v). The reduction percent peaked at 42.50% for tranexamic acid at 6% (w/v), 81.82% for tranexamic acid at 8% (w/v), and 99.82% for tranexamic acid at 10% (w/v) in the high virus inocula. Particular attention should be noted on the percent reduction of the tranexamic acid at 10%

TABLE 11

| Sample | Virus Inocula | Replicate Number | Contact Time | Titer (Log$_{10}$TCID$_{50}$/mL) |
|---|---|---|---|---|
| Cell viability/media sterility control | NA | NA | NA | no virus was detected, cells were viable; media sterile |
| Virus Stock Titer Control | High | | | 5.50 ± 0.00 |
| Input Virus Control (0% Tranexamic Acid) | High | 1 | 72 ± 8 hours | 6.00 ± 0.28 |
| | | 2 | | 6.00 ± 0.28 |
| | | 3 | | 7.00 ± 0.28 |
| | | 4 | | 7.00 ± 0.28 |
| | Input Virus Control (High) - Average | | | 6.74 ± 0.28 |
| 6% Tranexamic Acid | High | 1 | 72 ± 8 hours | 6.75 ± 0.25 |
| | | 2 | | 6.75 ± 0.25 |
| | | 3 | | 7.00 ± 0.28 |
| | | 4 | | 6.50 ± 0.35 |
| 8% Tranexamic Acid | High | 1 | | 6.00 ± 0.28 |
| | | 2 | | 6.25 ± 0.25 |
| | | 3 | | 6.50 ± 0.00 |
| | | 4 | | 6.00 ± 0.28 |
| 10% Tranexamic Acid | High | 1 | | 4.00 ± 0.28 |
| | | 2 | | 4.25 ± 0.37 |
| | | 3 | | 5.50 ± 0.00 |
| | | 4 | | 4.50 ± 0.00 |

The resulting reduction factors are shown below in Table 12, where the input virus control average was used as the input viral titer, the low virus inocula was $10^{3.0}$ TCID$_{50}$/mL, (w/v), especially as indicated in both the low and high virus inocula, where a reduction greater than 99% is demonstrated.

TABLE 12

| Test Article | Virus Inocula | Replicate Number | Contact Time | Input Viral Titer (Log$_{10}$TCID$_{50}$) | Output Viral Titer (Log$_{10}$TCID$_{50}$) | Log$_{10}$ Reduction | Reduction (%) |
|---|---|---|---|---|---|---|---|
| 6% Tranexamic Acid | Low | 1 | 48 ± 8 hours | 7.64 | 7.00 | 0.64 | 77.30 |
| | | 2 | | 7.64 | 6.50 | 1.14 | 92.82 |
| | | 3 | | 7.64 | 6.75 | 0.89 | 87.24 |
| | | 4 | | 7.64 | 6.25 | 1.39 | 95.96 |
| 8% Tranexamic Acid | | 1 | | 7.64 | 4.75 | 2.89 | 99.87 |
| | | 2 | | 7.64 | 4.00 | 3.64 | 99.98 |
| | | 3 | | 7.64 | 4.25 | 3.39 | 99.96 |
| | | 4 | | 7.64 | 5.25 | 2.39 | 99.60 |
| 10% Tranexamic Acid | | 1 | | 7.64 | 4.25 | 3.39 | 99.96 |
| | | 2 | | 7.64 | 3.75 | 3.89 | 99.99 |
| | | 3 | | 7.64 | 4.25 | 3.39 | 99.96 |
| | | 4 | | 7.64 | 4.25 | 3.39 | 99.96 |

TABLE 12-continued

| Test Article | Virus Inocula | Replicate Number | Contact Time | Input Viral Titer ($Log_{10}TCID_{50}$) | Output Viral Titer ($Log_{10}TCID_{50}$) | $Log_{10}$ Reduction | Reduction (%) |
|---|---|---|---|---|---|---|---|
| 6% Tranexamic Acid | High | 1 | 48 ± 8 hours | 6.74 | 6.75 | −0.01 | No reduction |
| | | 2 | | 6.74 | 6.75 | −0.01 | No reduction |
| | | 3 | | 6.74 | 7.00 | −0.26 | No reduction |
| | | 4 | | 6.74 | 6.50 | 0.24 | 42.50 |
| 8% Tranexamic Acid | | 1 | | 6.74 | 6.00 | 0.74 | 81.82 |
| | | 2 | | 6.74 | 6.25 | 0.49 | 67.67 |
| | | 3 | | 6.74 | 6.50 | 0.24 | 42.50 |
| | | 4 | | 6.74 | 6.00 | 0.74 | 81.82 |
| 10% Tranexamic Acid | | 1 | | 6.74 | 4.00 | 2.74 | 99.82 |
| | | 2 | | 6.74 | 4.25 | 2.49 | 99.68 |
| | | 3 | | 6.74 | 5.50 | 1.24 | 94.25 |
| | | 4 | | 6.74 | 4.50 | 2.24 | 99.43 |

Antiviral Activity of Tranexamic Acid/L-Arginine Against Herpes Simplex Virus Type 1 (HSV-1)

Each sample tested and shown below each had 3 replicates and consisted of an input virus control (no extraneous tranexamic acid or L-arginine), tranexamic acid at 2% (w/v), 5,000 μM L-arginine, 10,000 μM L-arginine, 25,000 μM L-arginine, and mixtures of 2% (w/v) tranexamic acid with 5,000 μM L-arginine, 10,000 μM L-arginine, and 25,000 μM L-arginine, each. Tranexamic acid with L-arginine mixtures were prepared with double concentration values of each component and diluted with equal amounts of each component to obtain the final concentrations as indicated above. Contact time for each sample was 48±8 hours and reduction factors were generated using input viral titer ($Log_{10}TCID_{50}$) and output viral titer ($Log_{10}TCID_{50}$) resulting in correlated reduction percentages or promotion percentages with corresponding $Log_{10}$ titer differences indicated.

Preparation for evaluation of antiviral activity of tranexamic acid/L-arginine against HSV-1 was prepared as follows: 0.25 mL of virus inoculum (containing $10^{3.0}$ $TCID_{50}$ units) was added to 3 wells for each dose of tranexamic acid, L-arginine, tranexamic acid with L-arginine, or input virus control. 1.0 mL of each dose of tranexamic acid, L-arginine, tranexamic acid with L-arginine, or DM (for input virus control) was added to each well. The plate was incubated for 48±8 hours at 36±2° C. with 5±3% $CO_2$. The plate was then frozen at −60 to −90° C. for 1 day, thawed, and the contents of each well centrifuged at 2,000 RPM for 10 minutes. The supernatant from each well was collected and assayed for infectious virus.

Titer results are depicted in Table 13 below, the input virus control titer ($Log_{10}TCID_{50}$/mL) for the virus inocula ranged from 6.25±0.11 to 6.55±0.12 with an average of 6.39±0.10, with the virus stock titer control having a titer of 3.68±0.20. Sample amounts of tranexamic acid at 2% (w/v), 5,000 μM L-arginine, 10,000 μM L-arginine, 25,000 μM L-arginine, and mixtures of 2% (w/v) tranexamic acid with 5,000 μM L-arginine, 10,000 μM L-arginine, and 25,000 μM L-arginine, having titer values ($Log_{10}TCID_{50}$/mL) as indicated below, were used in the testing.

TABLE 13

| Sample | Replicate Number | Contact Time | Titer ($Log_{10}TCID_{50}$/mL) |
|---|---|---|---|
| Cell viability/media sterility control | NA | NA | no virus was detected, cells were viable; media sterile |
| Virus Stock Titer Control | | | 3.68 ± 0.20 |
| Input Virus Control (No extraneous Tranexamic Acid or L-Arginine) | 1 | 48 ± 8 hours | 6.31 ± 0.08 |
| | 2 | | 6.55 ± 0.12 |
| | 3 | | 6.25 ± 0.11 |
| Input Virus Control - Average | | | 6.39 ± 0.10 |
| 2% Tranexamic Acid (TA) | 1 | 48 ± 8 hours | 5.24 ± 0.08 |
| | 2 | | 5.30 ± 0.10 |
| | 3 | | 5.12 ± 0.10 |
| 5,000 μM L-Arginine | 1 | 48 ± 8 hours | 6.73 ± 0.06 |
| | 2 | | 6.73 ± 0.06 |
| | 3 | | 6.43 ± 0.12 |
| 10,000 μM L-Arginine | 1 | | 7.21 ± 0.06 |
| | 2 | | 7.09 ± 0.09 |
| | 3 | | 7.15 ± 0.08 |
| 25,000 μM L-Arginine | 1 | | 7.21 ± 0.06 |
| | 2 | | 6.97 ± 0.09 |
| | 3 | | 6.85 ± 0.06 |
| 2% TA + 5,000 μM L-Arginine | 1 | 48 ± 8 hours | 5.71 ± 0.13 |
| | 2 | | 5.48 ± 0.08 |
| | 3 | | 5.71 ± 0.10 |

TABLE 13-continued

| Sample | Replicate Number | Contact Time | Titer ($Log_{10}TCID_{50}$/mL) |
|---|---|---|---|
| 2% TA + 10,000 µM L-Arginine | 1 | | 4.52 ± 0.12 |
| | 2 | | 4.94 ± 0.10 |
| | 3 | | 4.58 ± 0.09 |
| 2% TA + 25,000 µM L-Arginine | 1 | | 2.61 ± 0.10 |
| | 2 | | 2.43 ± 0.11 |
| | 3 | | 3.21 ± 0.09 |

The resulting reduction factors are shown below in Table 14, where the input virus control average was used as the input viral titer. As can be seen in Table 14, the reduction percentage peaked at 95% for tranexamic acid at 2% (w/v), while the samples containing L-Arginine (at 5,000 µM, 10,000 µM, and 25,000 µM) showed no viral reduction, but rather, showed viral promotion. Viral promotion peaked at 54% for 5,000 µM L-arginine, 85% for 10,000 µM L-arginine, and 85% for 25,000 µM L-arginine. Samples containing 2% (w/v) tranexamic acid with L-arginine demonstrated contrasting results compared to samples containing only L-arginine in viral reduction. Viral reduction peaked at 88% for 2% (w/v) tranexamic acid with 5,000 µM L-arginine, 99% for 2% (w/v) tranexamic acid with 10,000 µM L-arginine, and 99.99% for 2% (w/v) tranexamic acid with 25,000 µM L-arginine. As demonstrated in the data presented below, 2% (w/v) tranexamic acid with 25,000 µM L-arginine showed greater than 99% viral reduction.

factors were generated using input viral titer ($Log_{10}TCID_{50}$) and output viral titer ($Log_{10}TCID_{50}$) resulting in correlated reduction percentages or promotion percentages with corresponding $Log_{10}$ titer differences indicated.

Preparation for evaluation of antiviral activity of tranexamic acid/L-arginine against HSV-2 was prepared as follows: 0.25 mL of virus inoculum (containing $10^{3.0}$ $TCID_{50}$ units) was added to 3 wells for each dose of tranexamic acid, L-arginine, tranexamic acid with L-arginine, or input virus control. 1.0 mL of each dose of tranexamic acid, L-arginine, tranexamic acid with L-arginine, or DM (for input virus control) was added to each well. The plate was incubated for 48±8 hours at 36±2° C. with 5±3% $CO_2$. The plate was then frozen at −60 to −90° C. for 1 day, thawed, and the contents of each well centrifuged at

TABLE 14

| Test Article | Replicate Number | Contact Time | Input Viral Titer ($Log_{10}TCID_{50}$) | Output Viral Titer ($Log_{10}TCID_{50}$) | $Log_{10}$ Titer Difference | Viral Reduction (%) | Viral Promotion (%) |
|---|---|---|---|---|---|---|---|
| 2% Tranexamic Acid (TA) | 1 | 48 ± 8 hours | 6.39 | 5.24 | −1.15 | 93 | NA |
| | 2 | | 6.39 | 5.30 | −1.09 | 92 | |
| | 3 | | 6.39 | 5.12 | −1.27 | 95 | |
| 5,000 µM L-Arginine | 1 | | 6.39 | 6.73 | 0.34 | NA | 54 |
| | 2 | | 6.39 | 6.73 | 0.34 | | 54 |
| | 3 | | 6.39 | 6.43 | 0.04 | | 9 |
| 10,000 µM L-Arginine | 1 | | 6.39 | 7.21 | 0.82 | | 85 |
| | 2 | | 6.39 | 7.09 | 0.70 | | 80 |
| | 3 | | 6.39 | 7.15 | 0.76 | | 83 |
| 25,000 µM L-Arginine | 1 | | 6.39 | 7.21 | 0.82 | | 85 |
| | 2 | | 6.39 | 6.97 | 0.58 | | 74 |
| | 3 | | 6.39 | 6.85 | 0.46 | | 65 |
| 2% TA + 5,000 µM L-Arginine | 1 | 48 ± 8 hours | 6.39 | 5.71 | −0.68 | 79 | NA |
| | 2 | | 6.39 | 5.48 | −0.91 | 88 | |
| | 3 | | 6.39 | 5.71 | −0.68 | 79 | |
| 2% TA + 10,000 µM L-Arginine | 1 | | 6.39 | 4.52 | −1.87 | 99 | |
| | 2 | | 6.39 | 4.94 | −1.45 | 96 | |
| | 3 | | 6.39 | 4.58 | −1.81 | 98 | |
| 2% TA + 25,000 µM L-Arginine | 1 | | 6.39 | 2.61 | −3.78 | 99.98 | |
| | 2 | | 6.39 | 2.43 | −3.96 | 99.99 | |
| | 3 | | 6.39 | 3.21 | −3.18 | 99.9 | |

Antiviral Activity of Tranexamic Acid/L-Arginine Against Herpes Simplex Virus Type 2 (HSV-2)

Each sample tested and shown below each had 3 replicates and consisted of an input virus control (no extraneous tranexamic acid or L-arginine), tranexamic acid at 2% (w/v), 5,000 µM L-arginine, 10,000 µM L-arginine, 25,000 µM L-arginine, and mixtures of 2% (w/v) tranexamic acid with 5,000 µM L-arginine, 10,000 µM L-arginine, and 25,000 µM L-arginine, each. Tranexamic acid with L-arginine mixtures were prepared with double concentration values of each component and diluted with equal amounts of each component to obtain the final concentrations as indicated above. Contact time for each sample was 48±8 hours and reduction 2,000 RPM for 10 minutes. The supernatant from each well was collected and assayed for infectious virus.

Titer results are depicted in Table 15 below, the input virus control titer ($Log_{10}TCID_{50}$/mL) for the virus inocula ranged from 4.82±0.11 to 5.00±0.13 with an average of 4.93±0.10, with the virus stock titer control having a titer of 3.18±0.18. Sample amounts of tranexamic acid at 2% (w/v), 5,000 µM L-arginine, 10,000 µM L-arginine, 25,000 µM L-arginine, and mixtures of 2% (w/v) tranexamic acid with 5,000 µM L-arginine, 10,000 µM L-arginine, and 25,000 µM L-arginine, having titer values ($Log_{10}TCID_{50}$/mL) as indicated below, were used in the testing.

TABLE 15

| Sample | Replicate Number | Contact Time | Titer ($Log_{10}TCID_{50}$/mL) |
|---|---|---|---|
| Cell viability/media sterility control | NA | NA | no virus was detected, cells were viable; media sterile |
| Virus Stock Titer Control | | | 3.18 ± 0.18 |
| Input Virus Control (No extraneous Tranexamic Acid or L-Arginine) | 1 | 48 ± 8 hours | 5.00 ± 0.13 |
| | 2 | | 4.82 ± 0.11 |
| | 3 | | 4.94 ± 0.06 |
| Input Virus Control - Average | | | 4.93 ± 0.10 |
| 2% Tranexamic Acid (TA) | 1 | 48 ± 8 hours | 2.55 ± 0.10 |
| | 2 | | 2.43 ± 0.10 |
| | 3 | | 2.79 ± 0.12 |
| 5,000 μM L-Arginine | 1 | 48 ± 8 hours | 5.54 ± 0.11 |
| | 2 | | 5.18 ± 0.09 |
| | 3 | | 4.76 ± 0.08 |
| 10,000 μM L-Arginine | 1 | | 5.36 ± 0.11 |
| | 2 | | 4.94 ± 0.06 |
| | 3 | | 5.54 ± 0.09 |
| 25,000 μM L-Arginine | 1 | | 4.94 ± 0.10 |
| | 2 | | 4.46 ± 0.06 |
| | 3 | | 4.94 ± 0.06 |
| 2% TA + 5,000 μM L-Arginine | 1 | 48 ± 8 hours | 2.37 ± 0.10 |
| | 2 | | 2.20 ± 0.09 |
| | 3 | | 2.49 ± 0.13 |
| 2% TA + 10,000 μM L-Arginine | 1 | | 2.08 ± 0.06 |
| | 2 | | 2.14 ± 0.08 |
| | 3 | | 2.20 ± 0.09 |
| 2% TA + 25,000 μM L-Arginine | 1 | | 1.54 ± 0.00 |
| | 2 | | 1.60 ± 0.06 |
| | 3 | | 1.54 ± 0.00 |

The resulting reduction factors are shown below in Table 16, where the input virus control average was used as the input viral titer. As can be seen in Table 16, the reduction percentage peaked at 99.7% for tranexamic acid at 2% (w/v), while samples containing L-arginine (at 5,000 μM, 10,000 μM, and 25,000 μM) showed mostly viral promotion, except as noted in replicate 3 of the 5,000 μM L-arginine sample and replicate 2 of the 25,000 μM L-arginine sample, which showed a viral reduction of 32% and 66%, respectively. Viral promotion peaked at 76% for 5,000 μM L-arginine, 76% for 10,000 μM L-arginine, and 3% for 25,000 μM L-arginine. Samples containing 2% (w/v) tranexamic acid with L-arginine demonstrated contrasting results compared to samples containing only L-arginine in viral reduction. Viral reduction peaked at 99.8% for 2% (w/v) tranexamic acid with 5,000 μM L-arginine, 99.9% for 2% (w/v) tranexamic acid with 10,000 μM L-arginine, and 99.96% for 2% (w/v) tranexamic acid with 25,000 μM L-arginine. As demonstrated in the data presented below, 2% (w/v) tranexamic acid with L-arginine (at 5,000 μM, 10,000 μM, and 25,000 μM) showed greater than 99% viral reduction.

TABLE 16

| Test Article | Replicate Number | Contact Time | Input Viral Titer ($Log_{10}TCID_{50}$) | Output Viral Titer ($Log_{10}TCID_{50}$) | $Log_{10}$ Titer Difference | Viral Reduction (%) | Viral Promotion (%) |
|---|---|---|---|---|---|---|---|
| 2% Tranexamic Acid (TA) | 1 | 48 ± 8 hours | 4.93 | 2.55 | −2.38 | 99.6 | NA |
| | 2 | | 4.93 | 2.43 | −2.50 | 99.7 | |
| | 3 | | 4.93 | 2.79 | −2.14 | 99.3 | |
| 5,000 μM L-Arginine | 1 | | 4.93 | 5.54 | 0.61 | NA | 76 |
| | 2 | | 4.93 | 5.18 | 0.25 | NA | 44 |
| | 3 | | 4.93 | 4.76 | −0.17 | 32 | NA |
| 10,000 μM L-Arginine | 1 | | 4.93 | 5.36 | 0.43 | NA | 63 |
| | 2 | | 4.93 | 4.94 | 0.01 | NA | 3 |
| | 3 | | 4.93 | 5.54 | 0.61 | NA | 76 |
| 25,000 μM L-Arginine | 1 | | 4.93 | 4.94 | 0.01 | NA | 3 |
| | 2 | | 4.93 | 4.46 | −0.47 | 66 | NA |
| | 3 | | 4.93 | 4.94 | 0.01 | NA | 3 |
| 2% TA + 5,000 μM L-Arginine | 1 | 48 ± 8 hours | 4.93 | 2.37 | −2.56 | 99.7 | NA |
| | 2 | | 4.93 | 2.20 | −2.73 | 99.8 | |
| | 3 | | 4.93 | 2.49 | −2.44 | 99.6 | |
| 2% TA + 10,000 μM L-Arginine | 1 | | 4.93 | 2.08 | −2.85 | 99.9 | |
| | 2 | | 4.93 | 2.14 | −2.79 | 99.8 | |
| | 3 | | 4.93 | 2.20 | −2.73 | 99.8 | |
| 2% TA + 25,000 μM L-Arginine | 1 | | 4.93 | 1.54 | −3.39 | 99.96 | |
| | 2 | | 4.93 | 1.60 | −3.33 | 99.95 | |
| | 3 | | 4.93 | 1.54 | −3.39 | 99.96 | |

Antiviral Activity of Tranexamic Acid Against Herpes Simplex Virus Type 1 (HSV-1) Using Arginine and Histidine Each sample tested and shown below each had 3 replicates and consisted of an input virus control (no extraneous compounds), tranexamic acid at 2% (w/v), 0.5 mM L-arginine, 2 mM L-arginine, 5 mM L-arginine, and mixtures of 2% (w/v) tranexamic acid with 0.5 mM L-arginine, 2 mM L-arginine, and 5 mM L-arginine, each. Tranexamic acid with L-arginine mixtures were prepared with double concentration values of each component and diluted with equal amounts of each component to obtain the final concentrations as indicated above. Contact time for each sample was 48±2 hours and $Log_{10}$ titer reductions were generated using the input viral titer ($Log_{10}TCID_{50}$) and the output viral titer ($Log_{10}TCID_{50}$).

Preparation for evaluation of antiviral activity of tranexamic acid/L-arginine against HSV-1 was prepared as follows: 0.25 mL of virus inoculum (containing $10^{3.0}$ $TCID_{50}$ units) was added to 3 wells for each dose of tranexamic acid, L-arginine, tranexamic acid with L-arginine, or input virus control. 1.0 mL of each dose of tranexamic acid, L-arginine, tranexamic acid with L-arginine, or DM (for input virus control) was added to each well. The plate was incubated for 48±2 hours at 36±2° C. with 5±3% $CO_2$. The plate was then frozen at −60 to −90° C., thawed, and the contents of each well centrifuged at 2,000 RPM for 10 minutes. The supernatant from each well was collected and assayed for infectious virus.

Titer results are depicted in Table 17 below, the input virus control titer ($Log_{10}TCID_{50}$/mL) for the virus inocula ranged from 8.34±0.10 to 8.64±0.06 with an average of 8.50±0.09, with the virus stock titer control having a titer of 3.68±0.20. Sample amounts of tranexamic acid at 2% (w/v), 0.5 mM L-arginine, 2 mM L-arginine, 5 mM L-arginine, and mixtures of 2% (w/v) tranexamic acid with 0.5 mM L-arginine, 2 mM L-arginine, and 5 mM L-arginine, having titer values ($Log_{10}TCID_{50}$/mL) as indicated below, were used in the testing.

Each sample tested and shown below each had 3 replicates and consisted of 0.5 mM L-histidine, 1 mM L-histidine, 5 mM L-histidine, 10 mM L-histidine, 25 mM L-histidine, and mixtures of 2% (w/v) tranexamic acid with 0.01 mM L-histidine, 0.05 mM L-histidine, 0.1 mM L-histidine, 0.25 mM L-histidine, and 0.5 mM L-histidine each. Tranexamic acid with L-histidine mixtures were prepared with double concentration values of each component and diluted with equal amounts of each component to obtain the final concentrations as indicated above. Contact time for each sample was 48±2 hours and $Log_{10}$ titer reductions were generated using the input viral titer ($Log_{10}TCID_{50}$) and the output viral titer ($Log_{10}TCID_{50}$).

Preparation for evaluation of antiviral activity of tranexamic acid/L-histidine against HSV-1 was prepared as follows: 0.25 mL of virus inoculum (containing $10^{3.0}$ $TCID_{50}$ units) was added to 3 wells for each dose of L-histidine or tranexamic acid with L-histidine. 1.0 mL of each dose of L-histidine or tranexamic acid with L-histidine was added to each well. The plate was incubated for 48±2 hours at 36±2° C. with 5±3% $CO_2$. The plate was then frozen at −60 to −90° C., thawed, and the contents of each well centrifuged at 2,000 RPM for 10 minutes. The supernatant from each well was collected and assayed for infectious virus.

Titer results are depicted in Table 18 below. Sample amounts of 0.5 mM L-histidine, 1 mM L-histidine, 5 mM L-histidine, 10 mM L-histidine, 25 mM L-histidine, and mixtures of 2% (w/v) tranexamic acid with 0.01 mM L-histidine, 0.05 mM L-histidine, 0.1 mM L-histidine, 0.25 mM L-histidine, and 0.5 mM L-histidine, having titer values ($Log_{10}TCID_{50}$/mL) as indicated below, were used in the testing.

TABLE 17

| Sample | Replicate Number | Contact Time | Titer ($Log_{10}TCID_{50}$/mL) |
| --- | --- | --- | --- |
| Cell viability/media sterility control | NA | NA | no virus was detected, cells were viable; media sterile |
| Virus Stock Titer Control | | | 3.68 ± 0.20 |
| Input Virus Control | 1 | 48 ± 2 | 8.34 ± 0.10 |
| (No extraneous compounds) | 2 | hours | 8.46 ± 0.09 |
| | 3 | | 8.64 ± 0.06 |
| | Input Virus Control - Average | | 8.50 ± 0.09 |
| 2% Tranexamic Acid (TA) | 1 | 48 ± 2 | 7.15 ± 0.08 |
| | 2 | hours | 7.21 ± 0.06 |
| | 3 | | 7.27 ± 0.00 |
| 0.5 mM L-Arginine | 1 | | 8.52 ± 0.09 |
| | 2 | | 8.22 ± 0.11 |
| | 3 | | 8.34 ± 0.11 |
| 2 mM L-Arginine | 1 | | 8.46 ± 0.09 |
| | 2 | | 8.46 ± 0.10 |
| | 3 | | 8.64 ± 0.10 |
| 5 mM L-Arginine | 1 | | 8.64 ± 0.06 |
| | 2 | | 8.52 ± 0.10 |
| | 3 | | 8.70 ± 0.00 |
| 2% TA + 0.5 mM L-Arginine | 1 | | 7.74 ± 0.08 |
| | 2 | | 7.62 ± 0.08 |
| | 3 | | 7.68 ± 0.11 |
| 2% TA + 2 mM L-Arginine | 1 | | 7.80 ± 0.06 |
| | 2 | | 7.86 ± 0.08 |
| | 3 | | 7.62 ± 0.08 |
| 2% TA + 5 mM L-Arginine | 1 | | 7.09 ± 0.09 |
| | 2 | | 7.09 ± 0.09 |
| | 3 | | 7.03 ± 0.09 |

TABLE 18

| Sample | Replicate Number | Contact Time | Titer ($Log_{10}TCID_{50}$/mL) |
|---|---|---|---|
| 0.5 mM L-Histidine | 1 | 48 ± 2 hours | 8.46 ± 0.09 |
|  | 2 |  | 8.76 ± 0.06 |
|  | 3 |  | 8.76 ± 0.10 |
| 1 mM L-Histidine | 1 |  | 8.40 ± 0.11 |
|  | 2 |  | 8.76 ± 0.10 |
|  | 3 |  | 8.70 ± 0.11 |
| 5 mM L-Histidine | 1 |  | 8.52 ± 0.10 |
|  | 2 |  | 8.82 ± 0.08 |
|  | 3 |  | 8.64 ± 0.06 |
| 10 mM L-Histidine | 1 |  | 8.70 ± 0.00 |
|  | 2 |  | 8.64 ± 0.06 |
|  | 3 |  | 8.64 ± 0.06 |
| 25 mM L-Histidine | 1 |  | 8.64 ± 0.10 |
|  | 2 |  | 8.52 ± 0.12 |
|  | 3 |  | 8.70 ± 0.00 |
| 2% TA + 0.01 mM L-Histidine | 1 |  | 6.91 ± 0.08 |
|  | 2 |  | 6.73 ± 0.06 |
|  | 3 |  | 6.97 ± 0.09 |
| 2% TA + 0.05 mM L-Histidine | 1 |  | 6.97 ± 0.09 |
|  | 2 |  | 6.97 ± 0.09 |
|  | 3 |  | 7.15 ± 0.08 |
| 2% TA + 0.1 mM L-Histidine | 1 |  | 7.03 ± 0.09 |
|  | 2 |  | 7.15 ± 0.08 |
|  | 3 |  | 6.97 ± 0.09 |
| 2% TA + 0.25 mM L-Histidine | 1 |  | 7.15 ± 0.08 |
|  | 2 |  | 6.97 ± 0.09 |
|  | 3 |  | 6.91 ± 0.08 |
| 2% TA + 0.5 mM L-Histidine | 1 |  | 7.15 ± 0.08 |
|  | 2 |  | 6.61 ± 0.09 |
|  | 3 |  | 6.97 ± 0.09 |

Each sample tested and shown below each had 3 replicates and consisted of mixtures of 2% (w/v) tranexamic acid with 0.5 mM L-arginine and 0.5 mM L-histidine, 0.5 mM L-arginine and 5 mM L-histidine, 0.5 mM L-arginine and 10 mM L-histidine, 2 mM L-arginine and 0.05 mM L-histidine, 2 mM L-arginine and 0.5 mM L-histidine, 2 mM L-arginine and 5 mM L-histidine, 5 mM L-arginine and 0.05 mM L-histidine, 5 mM L-arginine and 0.5 mM L-histidine, and 5 mM L-arginine and 5 mM L-histidine each. Tranexamic acid with L-arginine and L-histidine mixtures were prepared with triple concentration values of each component and diluted with equal amounts of each component to obtain the final concentrations as indicated above. Contact time for each sample was 48±2 hours and $Log_{10}$ titer reductions were generated using the input viral titer ($Log_{10}TCID_{50}$) and the output viral titer ($Log_{10}TCID_{50}$).

Preparation for evaluation of antiviral activity of tranexamic acid with L-arginine and L-histidine against HSV-1 was prepared as follows: 0.25 mL of virus inoculum (containing $10^{3.0}$ $TCID_{50}$ units) was added to 3 wells for each dose of tranexamic acid with L-arginine and L-histidine. 1.0 mL of each dose of tranexamic acid with L-arginine and L-histidine was added to each well. The plate was incubated for 48±2 hours at 36±2° C. with 5±3% $CO_2$. The plate was then frozen at −60 to −90° C., thawed, and the contents of each well centrifuged at 2,000 RPM for 10 minutes. The supernatant from each well was collected and assayed for infectious virus.

Titer results are depicted in Table 19 below. Sample amounts of 2% (w/v) tranexamic acid with 0.5 mM L-arginine and 0.5 mM L-histidine, 0.5 mM L-arginine and 5 mM L-histidine, 0.5 mM L-arginine and 10 mM L-histidine, 2 mM L-arginine and 0.05 mM L-histidine, 2 mM L-arginine and 0.5 mM L-histidine, 2 mM L-arginine and 5 mM L-histidine, 5 mM L-arginine and 0.05 mM L-histidine, 5 mM L-arginine and 0.5 mM L-histidine, and 5 mM L-arginine and 5 mM L-histidine, having titer values ($Log_{10}TCID_{50}$/mL) as indicated below, were used in the testing.

TABLE 19

| Sample | Replicate Number | Contact Time | Titer ($Log_{10}TCID_{50}$/mL) |
|---|---|---|---|
| 2% TA + 0.5 mM L-Arginine + 0.5 mM L-Histidine | 1 | 48 ± 2 hours | 8.34 ± 0.08 |
|  | 2 |  | 8.28 ± 0.06 |
|  | 3 |  | 8.10 ± 0.08 |
| 2% TA + 0.5 mM L-Arginine + 5 mM L-Histidine | 1 |  | 7.92 ± 0.11 |
|  | 2 |  | 7.50 ± 0.09 |
|  | 3 |  | 7.68 ± 0.10 |
| 2% TA + 0.5 mM L-Arginine + 10 mM L-Histidine | 1 |  | 5.95 ± 0.10 |
|  | 2 |  | 5.77 ± 0.10 |
|  | 3 |  | 6.13 ± 0.09 |
| 2% TA + 2 mM L-Arginine + 0.05 mM L-Histidine | 1 |  | 7.56 ± 0.09 |
|  | 2 |  | 7.86 ± 0.08 |
|  | 3 |  | 8.10 ± 0.08 |

TABLE 19-continued

| Sample | Replicate Number | Contact Time | Titer ($Log_{10}TCID_{50}/mL$) |
|---|---|---|---|
| 2% TA + 2 mM L-Arginine + 0.5 mM L-Histidine | 1 | | 8.04 ± 0.09 |
| | 2 | | 7.50 ± 0.09 |
| | 3 | | 7.74 ± 0.00 |
| 2% TA + 2 mM L-Arginine + 5 mM L-Histidine | 1 | | 6.67 ± 0.10 |
| | 2 | | 7.38 ± 0.10 |
| | 3 | | 7.56 ± 0.09 |
| 2% TA + 5 mM L-Arginine + 0.05 mM L-Histidine | 1 | | 7.62 ± 0.08 |
| | 2 | | 7.98 ± 0.09 |
| | 3 | | 8.04 ± 0.09 |
| 2% TA + 5 mM L-Arginine + 0.5 mM L-Histidine | 1 | | 7.92 ± 0.09 |
| | 2 | | 7.98 ± 0.09 |
| | 3 | | 7.74 ± 0.08 |
| 2% TA + 5 mM L-Arginine + 5 mM L-Histidine | 1 | | 6.91 ± 0.08 |
| | 2 | | 7.03 ± 0.09 |
| | 3 | | 6.91 ± 0.08 |

The resulting $Log_{10}$ titer reduction, where the input virus control average was used as the input viral titer, for 2% (w/v) tranexamic acid, 0.5 mM L-arginine, 2 mM L-arginine, 5 mM L-arginine, and mixtures of 2% (w/v) tranexamic acid with 0.5 mM L-arginine, 2 mM L-arginine, and 5 mM L-arginine are shown below in Table 20. As shown below, the $Log_{10}$ titer reduction peaked at 1.29 for 2% (w/v) tranexamic acid, 0.28 for 0.5 mM L-arginine, 0.04 for 2 mM L-arginine, while 5 mM L-arginine showed no $Log_{10}$ titer reduction. Further, $Log_{10}$ titer reduction peaked at 0.88 for 2% (w/v) tranexamic acid with 0.5 mM L-arginine, 0.88 for 2% (w/v) tranexamic acid with 2 mM L-arginine, and 1.47 for 2% (w/v) tranexamic acid with 5 mM L-arginine.

TABLE 20

| Sample | Replicate Number | Contact Time | Input Viral Titer ($Log_{10}TCID_{50}$) | Output Viral Titer ($Log_{10}TCID_{50}$) | $Log_{10}$ Titer Reduction |
|---|---|---|---|---|---|
| 2% Tranexamic Acid (TA) | 1 | 48 ± 2 hours | 8.50 | 7.15 | 1.35 |
| | 2 | | 8.50 | 7.21 | 1.29 |
| | 3 | | 8.50 | 7.27 | 1.23 |
| 0.5 mM L-Arginine | 1 | | 8.50 | 8.52 | No reduction |
| | 2 | | 8.50 | 8.22 | 0.28 |
| | 3 | | 8.50 | 8.34 | 0.16 |
| 2 mM L-Arginine | 1 | | 8.50 | 8.46 | 0.04 |
| | 2 | | 8.50 | 8.46 | 0.04 |
| | 3 | | 8.50 | 8.64 | No reduction |
| 5 mM L-Arginine | 1 | | 8.50 | 8.64 | No reduction |
| | 2 | | 8.50 | 8.52 | No reduction |
| | 3 | | 8.50 | 8.70 | No reduction |
| 2% TA + 0.5 mM L-Arginine | 1 | | 8.50 | 7.74 | 0.76 |
| | 2 | | 8.50 | 7.62 | 0.88 |
| | 3 | | 8.50 | 7.68 | 0.82 |
| 2% TA + 2 mM L-Arginine | 1 | | 8.50 | 7.80 | 0.70 |
| | 2 | | 8.50 | 7.86 | 0.64 |
| | 3 | | 8.50 | 7.62 | 0.88 |
| 2% TA + 5 mM L-Arginine | 1 | | 8.50 | 7.09 | 1.41 |
| | 2 | | 8.50 | 7.09 | 1.41 |
| | 3 | | 8.50 | 7.03 | 1.47 |

The resulting $Log_{10}$ titer reduction, where the input virus control average was used as the input viral titer, for 0.5 mM L-histidine, 1 mM L-histidine, 5 mM L-histidine, and 10 mM L-histidine are shown below in Table 21. As shown below, the $Log_{10}$ titer reduction for L-histidine peaked at 0.04 for 0.5 mM L-histidine and 0.10 for 1 mM L-histidine, while the remaining samples showed no $Log_{10}$ titer reduction.

TABLE 21

| Sample | Replicate Number | Contact Time | Input Viral Titer ($Log_{10}TCID_{50}$) | Output Viral Titer ($Log_{10}TCID_{50}$) | $Log_{10}$ Titer Reduction |
|---|---|---|---|---|---|
| 0.5 mM L-Histidine | 1 | 48 ± 2 hours | 8.50 | 8.46 | 0.04 |
| | 2 | | 8.50 | 8.76 | No reduction |
| | 3 | | 8.50 | 8.76 | No reduction |
| 1 mM L-Histidine | 1 | | 8.50 | 8.40 | 0.10 |
| | 2 | | 8.50 | 8.76 | No reduction |
| | 3 | | 8.50 | 8.70 | No reduction |
| 5 mM L-Histidine | 1 | | 8.50 | 8.52 | No reduction |
| | 2 | | 8.50 | 8.82 | No reduction |
| | 3 | | 8.50 | 8.64 | No reduction |
| 10 mM L-Histidine | 1 | | 8.50 | 8.70 | No reduction |
| | 2 | | 8.50 | 8.64 | No reduction |
| | 3 | | 8.50 | 8.64 | No reduction |

The resulting $Log_{10}$ titer reduction, where the input virus control average was used as the input viral titer, for 2% (w/v) tranexamic acid with 0.01 mM L-histidine, 0.05 mM L-histidine, 0.1 mM L-histidine, 0.25 mM L-histidine, and 0.5 mM L-histidine are shown below in Table 22. As shown below, the $Log_{10}$ titer reduction peaked at 1.77 for 2% (w/v) tranexamic acid with 0.01 mM L-histidine, 1.53 for 2% (w/v) tranexamic acid with 0.05 mM L-histidine, 1.53 for 2% (w/v) tranexamic acid with 0.1 mM L-histidine, 1.59 for 2% (w/v) tranexamic acid with 0.25 mM L-histidine, and 1.89 for 2% (w/v) tranexamic acid with 0.5 mM L-histidine.

TABLE 22

| Sample | Replicate Number | Contact Time | Input Viral Titer ($Log_{10}TCID_{50}$) | Output Viral Titer ($Log_{10}TCID_{50}$) | $Log_{10}$ Titer Reduction |
|---|---|---|---|---|---|
| 2% TA + 0.01 mM L-Histidine | 1 | 48 ± 2 hours | 8.50 | 6.91 | 1.59 |
| | 2 | | 8.50 | 6.73 | 1.77 |
| | 3 | | 8.50 | 6.97 | 1.53 |
| 2% TA + 0.05 mM L-Histidine | 1 | | 8.50 | 6.97 | 1.53 |
| | 2 | | 8.50 | 6.97 | 1.53 |
| | 3 | | 8.50 | 7.15 | 1.35 |
| 2% TA + 0.1 mM L-Histidine | 1 | | 8.50 | 7.03 | 1.47 |
| | 2 | | 8.50 | 7.15 | 1.35 |
| | 3 | | 8.50 | 6.97 | 1.53 |
| 2% TA + 0.25 mM L-Histidine | 1 | | 8.50 | 7.15 | 1.35 |
| | 2 | | 8.50 | 6.97 | 1.53 |
| | 3 | | 8.50 | 6.91 | 1.59 |
| 2% TA + 0.5 mM L-Histidine | 1 | | 8.50 | 7.15 | 1.35 |
| | 2 | | 8.50 | 6.61 | 1.89 |
| | 3 | | 8.50 | 6.97 | 1.53 |

The resulting $Log_{10}$ titer reduction, where the input virus control average was used as the input viral titer, for 2% (w/v) tranexamic acid with 0.5 mM L-arginine and 0.5 mM L-histidine, 0.5 mM L-arginine and 5 mM L-histidine, 0.5 mM L-arginine and 10 mM L-histidine, 2 mM L-arginine and 0.05 mM L-histidine, 2 mM L-arginine and 0.5 mM L-histidine, 2 mM L-arginine and 5 mM L-histidine, 5 mM L-arginine and 0.05 mM L-histidine, 5 mM L-arginine and 0.5 mM L-histidine, and 5 mM L-arginine and 5 mM L-histidine are shown below in Table 23. As shown below, the $Log_{10}$ titer reduction peaked at 0.40 for 2% (w/v) tranexamic acid with 0.5 mM L-arginine and 0.5 mM L-histidine, 1.00 for 2% (w/v) tranexamic acid with 0.5 mM L-arginine and 5 mM L-histidine, 2.73 for 2% (w/v) tranexamic acid with 0.5 mM L-arginine and 10 mM L-histidine, 0.94 for 2% (w/v) tranexamic acid with 2 mM L-arginine and 0.05 mM L-histidine, 1.00 for 2% (w/v) tranexamic acid with 2 mM L-arginine and 0.5 mM L-histidine, 1.83 for 2% (w/v) tranexamic acid with 2 mM L-arginine and 5 mM L-histidine, 0.88 for 2% (w/v) tranexamic acid with 5 mM L-arginine and 0.05 mM L-histidine, 0.76 for 2% (w/v) tranexamic acid with 5 mM L-arginine and 0.5 mM L-histidine, and 1.59 for 2% (w/v) tranexamic acid with 5 mM L-arginine and 5 mM L-histidine.

TABLE 23

| Sample | Replicate Number | Contact Time | Input Viral Titer ($Log_{10}TCID_{50}$) | Output Viral Titer ($Log_{10}TCID_{50}$) | $Log_{10}$ Titer Reduction |
|---|---|---|---|---|---|
| 2% TA + 0.5 mM L-Arginine + 0.5 mM L-Histidine | 1 | 48 ± 2 hours | 8.50 | 8.34 | 0.16 |
| | 2 | | 8.50 | 8.28 | 0.22 |
| | 3 | | 8.50 | 8.10 | 0.40 |
| 2% TA + 0.5 mM L-Arginine + 5 mM L-Histidine | 1 | | 8.50 | 7.92 | 0.58 |
| | 2 | | 8.50 | 7.50 | 1.00 |
| | 3 | | 8.50 | 7.68 | 0.82 |

TABLE 23-continued

| Sample | Replicate Number | Contact Time | Input Viral Titer ($Log_{10}TCID_{50}$) | Output Viral Titer ($Log_{10}TCID_{50}$) | $Log_{10}$ Titer Reduction |
|---|---|---|---|---|---|
| 2% TA + 0.5 mM L-Arginine + 10 mM L-Histidine | 1 | | 8.50 | 5.95 | 2.55 |
| | 2 | | 8.50 | 5.77 | 2.73 |
| | 3 | | 8.50 | 6.13 | 2.37 |
| 2% TA + 2 mM L-Arginine + 0.05 mM L-Histidine | 1 | | 8.50 | 7.56 | 0.94 |
| | 2 | | 8.50 | 7.86 | 0.64 |
| | 3 | | 8.50 | 8.10 | 0.40 |
| 2% TA + 2 mM L-Arginine + 0.5 mM L-Histidine | 1 | | 8.50 | 8.04 | 0.46 |
| | 2 | | 8.50 | 7.50 | 1.00 |
| | 3 | | 8.50 | 7.74 | 0.76 |
| 2% TA + 2 mM L-Arginine + 5 mM L-Histidine | 1 | | 8.50 | 6.67 | 1.83 |
| | 2 | | 8.50 | 7.38 | 1.12 |
| | 3 | | 8.50 | 7.56 | 0.94 |
| 2% TA + 5 mM L-Arginine + 0.05 mM L-Histidine | 1 | | 8.50 | 7.62 | 0.88 |
| | 2 | | 8.50 | 7.98 | 0.52 |
| | 3 | | 8.50 | 8.04 | 0.46 |
| 2% TA + 5 mM L-Arginine + 0.5 mM L-Histidine | 1 | | 8.50 | 7.92 | 0.58 |
| | 2 | | 8.50 | 7.98 | 0.52 |
| | 3 | | 8.50 | 7.74 | 0.76 |
| 2% TA + 5 mM L-Arginine + 5 mM L-Histidine | 1 | | 8.50 | 6.91 | 1.59 |
| | 2 | | 8.50 | 7.03 | 1.47 |
| | 3 | | 8.50 | 6.91 | 1.59 |

Overview of Results

As shown above in the preceding discussion, reduced viral replication for HSV-1, HSV-2, HIV, and H3N2 have been demonstrated using tranexamic acid at varying percentages. Generally, in relation to HSV-1 and HSV-2, both in low and high virus inocula, tranexamic acid at 2.0% (w/v) shows the best results, though even at low percentages of tranexamic acid, HSV-1 showed high reduction percentages. In relation to HIV, tranexamic acid at higher percentages, for example 4.0% (w/v), showed very good results both at low and high virus inocula. In relation to H3N2, tranexamic acid antiviral performance was shown to be dose dependent and related to the viral load. For instance, tranexamic acid at 8% (w/v) and 10% (w/v) shows high reduction percentages in the low viral load ($10^{3.0}$ $TCID_{50}$/mL), while tranexamic acid at 10% (w/v) shows high reduction percentages in the high viral load ($10^{5.0}$ $TCID_{50}$/mL).

Furthermore, as demonstrated in the preceding discussion, the addition of arginine significantly improves on the antiviral performance of tranexamic acid in HSV-1 and HSV-2. In relation to HSV-1, data indicates that 2% (w/v) tranexamic acid with 10,000 µM L-arginine increases the viral reduction percentage to 99%, as opposed to a peak 95% reduction with 2% (w/v) tranexamic acid alone. Further, data shows that 2% (w/v) tranexamic acid with 25,000 µM L-arginine increases the viral reduction percentage to 99.99%. With respect to HSV-2, data indicates that 2% (w/v) tranexamic acid with L-arginine at 5,000 µM, 10,000 µM, and 25,000 µM demonstrate a viral reduction of greater than 99%.

The laboratory testing of tranexamic acid with arginine was designed to demonstrate the mechanism of action of tranexamic acid in inhibiting HSV-1 and HSV-2 replication by antagonizing arginine. Various amounts of arginine were added to the tranexamic acid-treated cells to see if this would rescue viral replication. Surprisingly, results indicated that tranexamic acid combined with arginine, at least at higher levels, inhibited the virus more than tranexamic acid alone. These results prompted further review.

Previous research has indicated that histidine is an important amino acid involved in herpes replication, followed by arginine, though later studies focused on lysine antagonizing arginine and not histidine. Lysine, arginine, and histidine are the three basic (non-acidic) amino acids, and their structures are very similar, with some people considering them analogs of each other, especially lysine and arginine.

Based on the laboratory data shown above, it is contemplated that an overabundance of one basic amino acid of the three basic amino acids might antagonize the other two basic amino acids. Moreover, it is contemplated that an overabundance of two basic amino acids will antagonize the third basic amino acid. Likewise, the same applies with analogs or mimetics, such as tranexamic acid, taking the place of lysine. Based on the preceding laboratory tests and studies, it is contemplated that tranexamic acid antagonizes arginine and histidine, while mixtures of tranexamic acid with arginine antagonize histidine, and mixtures of tranexamic acid with histidine antagonize arginine, at sufficient amounts. In essence, the addition of one or more amino acids to tranexamic acid can significantly improve the effectiveness of antiviral activity. This improved effectiveness is accomplished by the overabundance of amino acids antagonizing the other amino acid (e.g., tranexamic acid, acting as lysine, in combination with arginine antagonizes histidine).

The normal physiological concentrations of arginine and histidine inside cells are around 0.1 to 1 mM, or an average of approximately 0.5 mM. The herpes virus needs both approximately 0.5 mM arginine and 0.5 mM histidine to replicate efficiently, and at 0.5 mM each, arginine and histidine do not antagonize each other. However, the studies described above illustrate that tranexamic acid at 2% (w/v) antagonizes both arginine and histidine, reducing the effective available concentration of arginine and histidine vastly below 0.5 mM each. Without being bound by theory, it is believed that arginine could be the primary, or the most direct, target, while histidine may be the secondary, or indirect, target.

The studies illustrated above demonstrate that adding back 0.5 mM arginine helps to relieve the "blocking effect" of arginine, however, the histidine is still not recovered, therefore only partial rescue is present. Adding back 0.5 mM histidine does not help in rescue as the direct target arginine is still being "blocked." However, adding back both 0.5 mM arginine and 0.5 mM histidine relieves the action of tranexamic acid, and almost completely rescues the herpes virus replication.

Based on the studies above, indication is provided that both arginine and histidine at 10 mM or above (e.g., excessive as compared to physiological levels), begin to antagonize each other. As such, it is envisioned that, 2% (w/v) tranexamic acid with 10 or 25 mM arginine will show a higher level of viral inhibition than 2% (w/v) tranexamic acid alone. This is due to the 2% (w/v) tranexamic acid with 0.5 mM arginine and 10 mM histidine sample showing a higher level of viral inhibition than 2% (w/v) tranexamic acid alone. It should be noted that in the studies conducted, 2% (w/v) tranexamic acid with 10 mM histidine could not be evaluated due to cytotoxicity. Further, concentrations of arginine or histidine at 2 to 5 mM may be near borderline levels, as they may show some rescuing effect over the 2% (w/v) tranexamic acid.

It is envisioned that tranexamic acid in combination with one or more amino acids can increase the antiviral efficacy of tranexamic acid. Combinations can include, but are not limited to, tranexamic acid with aliphatic amino acids, aromatic amino acids, acidic amino acids, basic amino acids, neutral amino acids, unique amino acids, amino acid analogs or mimetics, or any combination thereof. Moreover, various combinations of tranexamic acid (or other synthetic lysine or mimetic) with amino acids are believed to allow for higher doses of the composition without toxicity.

It should be noted that the percentage of tranexamic acid used in these laboratory tests was limited by the particular cell medium used. For example, 2% (w/v) tranexamic acid was the maximum concentration of tranexamic acid that could be used for HSV-1 and HSV-2 without cytotoxicity, and 4% (w/v) tranexamic acid was the maximum concentration that could be used for HIV-1. However, in the human body, which exhibits different biological behaviors, for example, an active metabolism, much higher concentrations of synthetic lysine analogs can be used. Typical topical usage ranges from concentrations of 3 to 10% (w/v), and studies have indicated that concentrations of up to 30% (w/v) can be safely administered. Thus, the above-described laboratory tests provide strong evidence of effectiveness of tranexamic acid in suppressing these viruses, and even higher concentrations of synthetic lysine agents in clinical use are envisioned. Further, it has been demonstrated above that tranexamic acid with arginine can interfere in the activity of histidine by antagonizing histidine. This can allow for larger doses of tranexamic acid with arginine without cytotoxicity.

Treatment and Prophylactic Usage in Human Subjects

In addition to the laboratory tests described above, various treatment and prophylactic use studies have been conducted and recorded for human subjects. For example, treatment activity is illustrated via a 54 year old female subject with a history of recurrent outbreaks of cold sores on or near the lips. In this instance, the subject noticed the first signs of the outbreak, in this case, a red blemish with small white spots surrounding it along with associated tingling, pain, and sensitivity, and immediately applied a small amount, approximately 0.25 mL of an aqueous solution of 5% (w/v) tranexamic acid to the area via a simple swab. This practice was repeated 5 times over the course of 36 hours and surprisingly within that 36 hour period the cold sore had healed to the point that only a small red spot was visible, which was totally resolved shortly thereafter. This activity was a marked improvement in the typical duration of the subject's outbreaks, which usually lasted approximately 14 days, even when using a topical antiviral treatment, such as ABREVA®. While a 5% (w/v) concentration of tranexamic acid proved to be effective, a range of concentrations and total dosages delivered, such as, 0.5 to 30% (w/v) delivered in increments of 0.25 to 5 mL over the course of 1 to 14 days, for example, can prove beneficial as well.

In addition to the treatment study mentioned above, further studies have been conducted in which three human subjects with an experience of recurring cold sores, generally lasting for about 2 weeks, applied 3% (w/v) tranexamic acid topically several times a day upon detection of the beginning of an outbreak, and the symptoms of the outbreak resolved within 48 hours. A fourth subject with an experience of recurring cold sores, who usually applied ABREVA® for several days just to avoid a larger outbreak, applied 10% (w/v) tranexamic acid topically a single time upon feeling the onset of an outbreak and noticing a very small blister, and the following morning the blister was gone and the outbreak had ceased. Furthermore, one of the subjects applied either 3 or 10% (w/v) tranexamic acid to their face daily for approximately one year, and experienced only one cold sore outbreak during that year, rather than their usual experience of 3 to 5 outbreaks.

Moreover, there have been three instances where individuals who have applied a solution of 3% (w/v) tranexamic acid to their nasal passages and throat every 6 to 8 hours when they sensed the symptoms of a cold or influenza infection, and the symptoms resolved within 36 to 48 hours, rather than the usual duration of around 2 weeks.

Although various embodiments of the present disclosure have been illustrated in the accompanying Tables and described in the foregoing Detailed Description, it will be understood that the present disclosure is not limited to the embodiments disclosed herein, but is capable of numerous rearrangements, modifications, and substitutions without departing from the spirit of the disclosure as set forth herein.

The term "substantially" is defined as largely but not necessarily wholly what is specified, as understood by a person of ordinary skill in the art. In any disclosed embodiment, the terms "substantially," "approximately," "generally," and "about" may be substituted with "within [a percentage] of" what is specified, where the percentage includes 0.1, 1, 5, and 10 percent.

The foregoing outlines features of several embodiments so that those skilled in the art may better understand the aspects of the disclosure. Those skilled in the art should appreciate that they may readily use the disclosure as a basis for designing or modifying other methods and compositions for carrying out the same purposes and/or achieving the same advantages of the embodiments introduced herein. Those skilled in the art should also realize that such equivalent constructions do not depart from the spirit and scope of the disclosure, and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a," "an," and other singular terms are intended to include the plural forms thereof unless specifically excluded.

What is claimed is:

1. A method for treatment of viral infections, the method comprising:
   topically administering a solution consisting of 3 to 30% (w/v) of a synthetic lysine analog or mimetic to a subject suffering from an infection caused by a virus, wherein the topical administration consists of directly administering the synthetic lysine analog or mimetic to an area on the subject that shows signs of viral infection and is the only mode of administration of the synthetic lysine analog or mimetic to the subject, wherein the synthetic lysine analog or mimetic is an antiviral agent that antagonizes or competes with an amino acid or other biological agent required by a virus to replicate or spread, wherein the synthetic lysine analog or mimetic is tranexamic acid, epsilon-aminocaproic acid (EACA), or AZD 6564, and wherein the synthetic lysine analog or mimetic is the only antiviral agent administered to the subject;

treating tissue to which the synthetic lysine analog or mimetic is topically applied; and wherein the viral infection is caused by a human immunodeficiency virus.

2. The method of claim 1, wherein the solution is applied as part of a vehicle which adapts to human skin and mucosa.

3. The method of claim 2, wherein the vehicle is a gel.

4. The method of claim 2, wherein the vehicle is a cream.

5. The method of claim 2, wherein the vehicle is a lotion.

6. The method of claim 1, wherein the administering of the synthetic lysine analog or mimetic occurs at least once a day.

7. The method of claim 1, wherein the administering of the synthetic lysine analog or mimetic occurs on a weekly or semiweekly basis.

8. The method of claim 1, wherein the administering of the synthetic lysine analog or mimetic occurs on a monthly or semimonthly basis.

9. The method of claim 1, wherein the synthetic lysine analog or mimetic is administered with at least one amino acid.

10. The method of claim 1, wherein the synthetic lysine analog or mimetic is administered with at least one other natural or synthetic amino acid analog or mimetic.

11. The method of claim 1, wherein the solution is an aqueous solution.

* * * * *